United States Patent

Dannheim

Patent Number: 5,216,138
Date of Patent: Jun. 1, 1993

[54] WATER-SOLUBLE AZO COMPOUNDS SUITABLE AS FIBRE-REACTIVE DYESTUFFS

[75] Inventor: Jörg Dannheim, Frankfurt am Main, Fed. Rep. of Germany

[73] Assignee: Hoechst Aktiengesellschaft, Frankfurt am Main, Fed. Rep. of Germany

[21] Appl. No.: 800,551

[22] Filed: Nov. 27, 1991

[30] Foreign Application Priority Data

Dec. 1, 1990 [DE]  Fed. Rep. of Germany ....... 4038343
Sep. 18, 1991 [DE]  Fed. Rep. of Germany ....... 4131050

[51] Int. Cl.$^5$ ................. C09B 62/507; D06P 1/382
[52] U.S. Cl. ............................. 534/642; 534/582; 534/641; 534/887; 558/29; 558/396; 558/397; 560/250; 560/254; 564/416; 564/421; 564/440; 568/30; 568/44; 8/527; 8/549
[58] Field of Search .............................. 534/642

[56] References Cited

U.S. PATENT DOCUMENTS

2,670,265  2/1954  Heyna et al. ............... 534/642 X
3,441,614  4/1969  Asscher et al. ................. 544/299
5,047,529  9/1991  Patsch et al. ................... 544/52

FOREIGN PATENT DOCUMENTS

0654544  2/1965  Belgium .
0392351  10/1990  European Pat. Off. .

Primary Examiner—Mary C. Lee
Assistant Examiner—Fiona T. Powers
Attorney, Agent, or Firm—Connolly & Hutz

[57] ABSTRACT

There are described water soluble azo compounds conforming to the formula (1)

D—N=N—K         (1)

where D is a radical of the formula (2), (2a) or (2b)

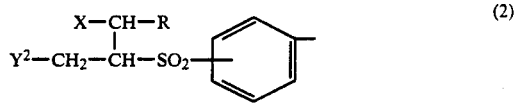

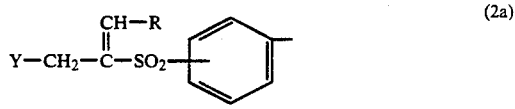

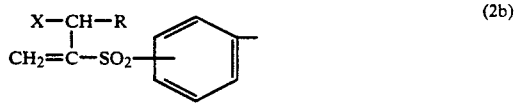

where Y is a substituent which is eliminable by alkali to form a vinyl group, $Y^2$ has one of the meanings of Y or is hydroxyl, X is chlorine or bromine, and R is hydrogen, lower alkyl, phenyl or halogen, and K is a radical of a singly couplable coupling component which may additionally contain an azo group, or the radical of a doubly couplable coupling component.

The compounds of the formula (1) have fiber-reactive properties and are very highly suitable for use as dyes for dyeing hydroxy- and/or carboxamido-containing material, in particular fiber material, for example cellulose-fiber materials, wool and synthetic polyamide fibers, in strong, fast shades.

There are also described novel starting compounds of the formulae (7), (7a) and (7b)

(Abstract continued on next page.)

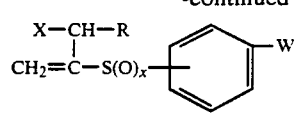 (7b)
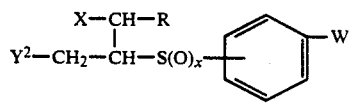 (7)
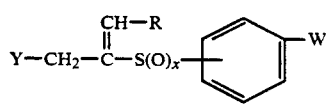 (7a)
where $Y^2$, X and R are each as defined above, x is zero or 2 and W is nitro or amino. The aniline compounds of the formula (7) obtainable from the compounds of the formula (7) where W is nitro by reduction of the nitro group can be used as diazo component for preparing the azo compounds of the formula (1).
16 Claims, No Drawings

WATER-SOLUBLE AZO COMPOUNDS SUITABLE AS FIBRE-REACTIVE DYESTUFFS

The present invention relates to the field of fiber reactive dyes.

Novel water soluble azo compounds conforming to the formula (1)

$$D-N=N-K \qquad (1)$$

have been found which possess useful fiber reactive dye properties.

In this formula (1) the meanings are as follows:

D is a radical of the formula (2), (2a) or (2b)

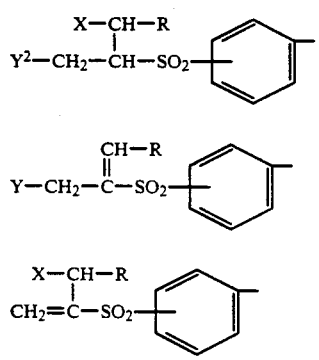

where

Y is a substituent which is eliminable by alkali to form a vinyl group, the sulfonyl group being attached to the benzene nucleus preferably meta or para to the free bond, $Y^2$ has one of the meanings of Y or is a hydroxyl group, the sulfonyl group being preferably bonded to the benzene nucleus meta or para to the free bond, X is chlorine or bromine, preferably chlorine, and R is hydrogen, alkyl of from 1 to 4 carbon atoms, phenyl or halogen, such as chlorine or bromine, but preferably hydrogen;

K is a radical of a singly couplable, preferably water soluble coupling component, which may additionally contain an azo group, or the radical of a doubly couplable, preferably water soluble coupling component, each selected from the series of the aminobenzenes, the phenols, in particular their sulfonic and carboxylic acids, the naphthols, in particular their sulfonic and carboxylic acids, the aminonaphthols, in particular their sulfonic acids, the acylaminonaphthols, in particular their sulfonic acids, having the acyl radical of an alkane- or alkene-carboxylic acid having from 1 to 4 or from 2 to 4 carbon atoms in the alkyl or alkenyl radical respectively or of an aromatic carboxylic acid, such as benzoic acid, or of an aromatic sulfonic acid, such as benzene- or toluene-sulfonic acid, or of an N-substituted carbamic acid, such as the N-phenylureido radical, or of from the series of the dihydroxynaphthalenesulfonic acids, the phenylazo and naphthylazo-aminonaphtholsulfonic acids, the 5-pyrazolones and 5-aminopyrazoles, the acetoacetylarylides, the 2-hydroxy-6-pyridones and the hydroxyquinolines, and K in addition to the substituents customary in dyes also contains a fiber reactive group of the formula $-SO_2-Y^1$, where $Y^1$ is vinyl or a group of the formula $-CH_2-CH_2-Y$, where Y has one of the above meanings.

Alkali eliminable substituents Y are for example halogen atoms, such as bromine and chlorine, cyano, trialkylammonium groups having alkyl groups of from 1 to 4 carbon atoms each, such as trimethylammonium and triethylammonium, ester groups of organic carboxylic and sulfonic acids, such as an alkanoyloxy radical of from 2 to 5 carbon atoms, for example acetyloxy, or a sulfobenzoyloxy, benzoyloxy, phenylsulfonyloxy or toluylsulfonyloxy radical, and phosphato, sulfato and thiosulfato. Preferably Y is chlorine.

Sulfo groups are groups conforming to the formula $-SO_3M$, carboxy groups are groups conforming to the formula $-COOM$, sulfato groups are groups conforming to the formula $-OSO_3M$, thiosulfato groups are groups conforming to the formula $-S-SO_3M$ and phosphato groups are groups conforming to the formula $-OPO_3M_2$, in each of which M is a hydrogen atom or a salt-forming metal atom, in particular an alkali metal atom, for example sodium, potassium or lithium.

Of the novel compounds of the formula (1), noteworthy compounds are for example those where K is a radical of the following formula (3a), (3b), (3c), (3d), (3e), (3f), (3g), (3h), (3i), (3k), (3m), (3n), (3p), (3q), (3r), (3s), (3t), (3v) and (3w):

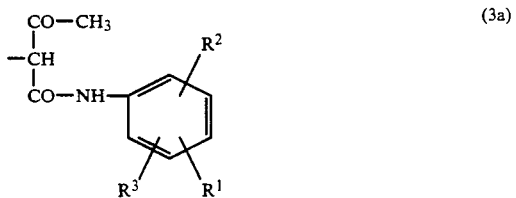

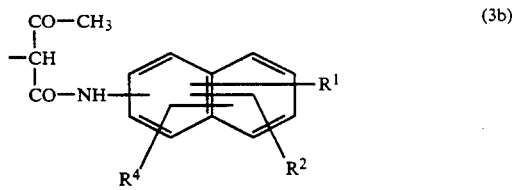

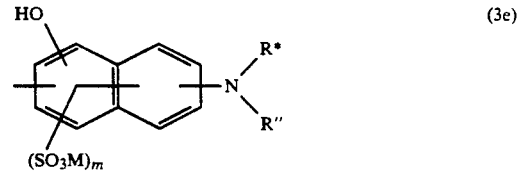

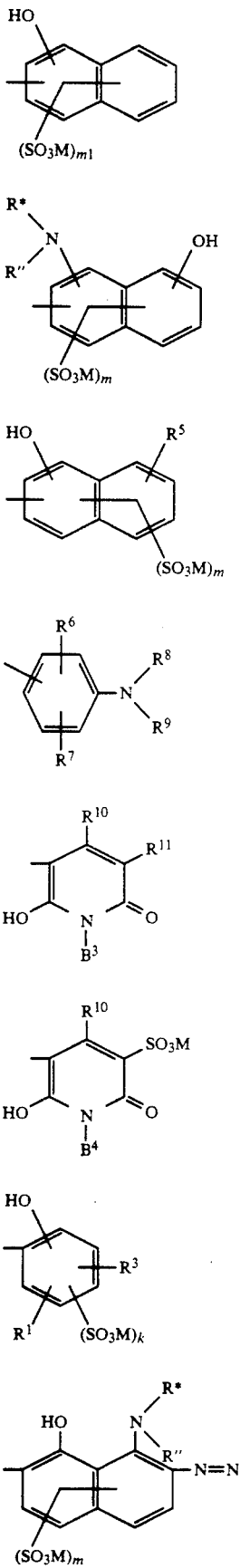
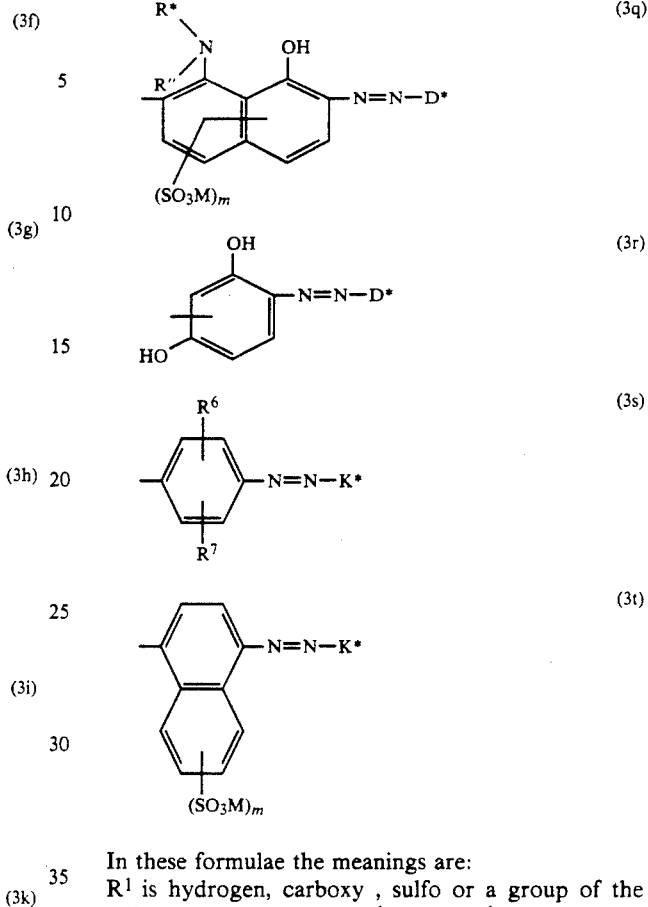

In these formulae the meanings are:

R¹ is hydrogen, carboxy, sulfo or a group of the formula —G*—SO₂—Y¹, where Y¹ has one of the abovementioned meanings and G* is a direct bond, a methylene or ethylene group or a propyleneoxy group of the formula —O—(CH₂)₃— or —O—CH₂—CH(CH₃)—;

R² is hydrogen, alkyl of from 1 to 4 carbon atoms, alkoxy of from 1 to 4 carbon atoms, chlorine, bromine, carboxy or sulfo, preferably hydrogen, alkyl of from 1 to 4 carbon atoms, alkoxy of from 1 to 4 carbon atoms, carboxy or sulfo;

R³ is hydrogen, alkyl of from 1 to 4 carbon atoms, alkoxy of from 1 to 4 carbon atoms, chlorine or bromine, preferably hydrogen or alkoxy of from 1 to 4 carbon atoms;

R⁴ is hydrogen, sulfo or carboxy, preferably hydrogen;

B¹ is alkyl of from 1 to 4 carbon atoms, in particular methyl, carboxy, carbalkoxy of from 2 to 5 carbon atoms, in particular carbomethoxy, carbamoyl, phenyl or phenyl which is substituted by 1 or 2 substituents selected from the group consisting of sulfo, carboxy, methyl, ethyl, methoxy, ethoxy and chlorine, and preferably is methyl, carboxy or carbalkoxy of from 2 to 5 carbon atoms;

B² is alkyl of from 1 to 4 carbon atoms, in particular methyl, carboxy, carbalkoxy of from 2 to 5 carbon atoms, carbamoyl, phenyl or phenyl which is substituted by 1 or 2 substituents selected from the group consisting of alkyl of from 1 to 4 carbon atoms, alkoxy of from 1 to 4 carbon atoms, chlorine, bromine and sulfo, and preferably is methyl or carboxy;

Q is phenyl which may be substituted, for example by 1, 2 or 3, preferably 1 or 2, substituents selected from the group consisting of chlorine, bromine, methyl, ethyl, methoxy, ethoxy, carboxy, sulfo and alkanoylamino of from 2 to 5 carbon atoms and/or by a group of the formula —$SO_2$—$Y^1$, where $Y^1$ is as defined above, or is naphthyl, which may be substituted by 1, 2 or 3 sulfo groups and optionally by 1 alkyl group of from 1 to 4 carbon atoms, 1 alkoxy group of from 1 to 4 carbon atoms, 1 chlorine atom or 1 alkanoylamino group of from 2 to 5 carbon atoms and/or by a group of the formula —$SO_2$—$Y^1$, where $Y^1$ is as defined above, but preferably is phenyl which is substituted by sulfo and/or by an —$SO_2$—$Y^1$ group;

$R^*$ is hydrogen or alkyl of from 1 to 4 carbon atoms, which may be substituted by phenyl or by phenyl which is substituted by sulfo and/or by —$SO_2$—$Y^1$, where $Y^1$ is as defined above, or is alkanoyl of from 2 to 5 carbon atoms, such as acetyl, or substituted or unsubstituted phenylsulfonyl or benzoyl, such as sulfobenzoyl, but preferably is hydrogen, acetyl, sulfobenzoyl or benzoyl;

$R''$ is hydrogen or alkyl of from 1 to 4 carbon atoms, such as ethyl or in particular methyl, which may be substituted by phenyl, sulfophenyl or a group of the formula —$SO_2$—$Y^1$, where $Y^1$ is as defined above, or is phenyl unsubstituted or substituted by 1 or 2 substituents selected from the group consisting of alkyl of from 1 to 4 carbon atoms, alkoxy of from 1 to 4 carbon atoms, chlorine, bromine, sulfo and —$SO_2$—$Y^1$, where $Y^1$ is as defined above, but preferably is alkyl of from 1 to 4 carbon atoms or in particular hydrogen;

$R^5$ is phenylureido, whose phenyl radical may be substituted by a group of the formula —$SO_2$—$Y^1$, where $Y^1$ is as defined above, or is alkanoylamino of from 2 to 5 carbon atoms, which may be substituted in the alkyl radical by a group of the formula —$SO_2$—$Y^1$, where $Y^1$ is as defined above, or is alkenoylamino of from 3 to 5 carbon atoms, such as acryloylamino, or is benzoylamino, which may be substituted by substituents selected from the group consisting of chlorine, methyl, methoxy, nitro, sulfo, carboxy and —$SO_2$—$Y^1$, where $Y^1$ is as defined above, but preferably is acetylamino or benzoylamino;

$R^6$ is hydrogen, alkyl of from 1 to 4 carbon atoms, alkoxy of from 1 to 4 carbon atoms, sulfo, carboxy, carbalkoxy of from 2 to 5 carbon atoms, halogen, such as bromine or chlorine, or alkoxy of from 1 to 4 carbon atoms which is substituted by hydroxy, acetyloxy, carboxy, carbamoyl, cyano or halogen, such as chlorine, but preferably is hydrogen, sulfo, methyl, ethyl, methoxy or ethoxy;

$R^7$ is hydrogen, alkyl of from 1 to 4 carbon atoms, alkoxy of from 1 to 4 carbon atoms, halogen, such as bromine or chlorine, cyano, trifluoromethyl, alkoxy of from 1 to 4 carbon atoms, which is substituted by hydroxy, acetyloxy, carboxy, carbamoyl, cyano or halogen, such as chlorine, or by a group of the formula —$SO_2$—$Y^1$, where $Y^1$ is as defined above, or is alkanoylamino of from 2 to 5 carbon atoms, such as acetylamino or propionylamino, which may be substituted by chlorine, bromine, alkoxy of from 1 to 4 carbon atoms, phenoxy, phenyl, hydroxy, carboxy or sulfo or a group of the formula —$SO_2$—$Y^1$, where $Y^1$ is as defined above, or is alkenoylamino of from 3 to 5 carbon atoms, which may be substituted by chlorine, bromine, carboxy or sulfo, or is benzoylamino, which may be substituted in the benzene nucleus, for example by substituents selected from the group consisting of chlorine, methyl, sulfo and a group of the formula —$SO_2$—$Y^1$, where $Y^1$ is as defined above, or is alkylsulfonyl of from 1 to 4 carbon atoms or phenylsulfonyl, which may be substituted in the benzene nucleus, for example by substituents selected from the group consisting of chlorine, methyl, sulfo and a group of the formula —$SO_2$—$Y^1$, where $Y^1$ is as defined above, or is alkylsulfonylamino of from 1 to 4 carbon atoms, which may be substituted by hydroxy, sulfato, chlorine, bromine, alkoxy of from 1 to 4 carbon atoms or a group of the formula —$SO_2$—$Y^1$, where $Y^1$ is as defined above, or is phenylsulfonylamino, which may be substituted in the benzene nucleus, for example by substituents selected from the group consisting of chlorine, methyl, sulfo and a group of the formula —$SO_2$—$Y^1$, where $Y^1$ is as defined above, or is carbamoyl, which may be monosubstituted or disubstituted on the nitrogen atom by 1 or 2 substituents, which substituents belong to the group consisting of alkyl of from 1 to 4 carbon atoms, alkyl of from 1 to 4 carbon atoms which is substituted (for example by hydroxy, sulfo, carboxy, sulfato, phenyl or a group of the formula —$SO_2$—$Y^1$, where $Y^1$ is as defined above), cycloalkyl of from 5 to 8 carbon atoms, phenyl and phenyl which is substituted, for example by substituents selected from the group consisting of chlorine, sulfo, methyl, methoxy, carboxy and a group of the formula —$SO_2$—$Y^1$, where $Y^1$ is as defined above, or is sulfamoyl, which may be mono- or disubstituted on the nitrogen atom by 1 or 2 substituents, which substituents belong to the group consisting of alkyl of from 1 to 4 carbon atoms, alkyl of from 1 to 4 carbon atoms which is substituted (for example by hydroxy, sulfo, carboxy, sulfato, phenyl or a group of the formula —$SO_2$—$Y^1$, where $Y^1$ is as defined above), cycloalkyl of from 5 to 8 carbon atoms, phenyl and phenyl which is substituted (for example by substituents selected from the group consisting of chlorine, sulfo, methyl, methoxy, carboxy and a group of the formula —$SO_2$—$Y^1$, where $Y^1$ is as defined above), or is ureido or ureido which is mono- or disubstituted at the terminal nitrogen atom by 1 or 2 substituents, which substituents belong to the group consisting of alkyl of from 1 to 4 carbon atoms, alkyl of from 1 to 4 carbon atoms which is substituted, for example by hydroxy, sulfo, carboxy, sulfato, phenyl or a group of the formula —$SO_2$—$Y^1$, where $Y^1$ is as defined above, cycloalkyl of from 5 to 8 carbon atoms, phenyl and phenyl which is substituted (for example by substituents selected from the group consisting of chlorine, sulfo, methyl, methoxy, carboxy and a group of the formula —$SO_2$—$Y^1$, where $Y^1$ is as defined above), but preferably is hydrogen, methyl, ethyl, methoxy, ethoxy, chlorine, amino, substituted amino, alkanoylamino of from. 2 to 5 carbon atoms, benzoylamino or phenylsulfonylamino or in particular ureido, acetylamino or benzoylamino;

$R^8$ is hydrogen or alkyl of from 1 to 4 carbon atoms, such as methyl or ethyl, which may be substituted for example by hydroxy, sulfo, carboxy, sulfato, a group of the formula —$SO_2$—$Y^1$, where $Y^1$ is as defined above, phenyl or sulfophenyl, or is alkenyl of from 2 to 4 carbon atoms, which may be substituted by carboxy, sulfo, chlorine or bromine, or is cycloalkyl of from 5 to 8 carbon atoms, but preferably is hydrogen, methyl, ethyl or hydroxy -, sulfo-, sulfato- or carboxy -substituted alkyl of from 2 to 4 carbon atoms, such as β-sulfatoethyl or β-sulfoethyl;

$R^9$ is hydrogen or alkyl of from 1 to 4 carbon atoms, which may be substituted, for example by hydroxy, sulfo, carboxy, sulfato, phenyl or —SO$_2$—Y$^1$, where Y$^1$ is as defined above, or is alkenyl of from 2 to 5 carbon atoms, which may be substituted by carboxy, sulfo or —SO$_2$—Y$^1$, where Y$^1$ is as defined above, or by chlorine or bromine, or R$^9$ is cycloalkyl of from 5 to 8 carbon atoms or phenyl, which may be substituted, for example by substituents selected from the group consisting of chlorine, sulfo, methyl, methoxy, carboxy and —SO$_2$—Y$^1$, where Y$^1$ is as defined above, or is naphthyl which is substituted by 1, 2 or 3 sulfo groups or by 1 or 2 sulfo groups and 1 or 2 groups of the formula —SO$_2$—Y$^1$, where Y$^1$ is as defined above, or only by one such group —SO$_2$—Y$^1$, but preferably is hydrogen, methyl, ethyl or alkyl of from 2 to 4 carbon atoms, which is substituted by hydroxy, sulfo, sulfato or carboxy, such as β-sulfatoethyl or β-sulfoethyl, or R$^8$ and R$^9$ together with the nitrogen atom and with or without a further hetero atom or a hetero group, such as N, O, S or NH, are a 5- to 8-membered, preferably saturated, heterocyclic radical, for example N-piperidino, N-morpholino or N-piperazino;

R$^{10}$ is hydrogen or alkyl of from 1 to 4 carbon atoms or alkyl of from 1 to 4 carbon atoms which is substituted by alkoxy of from 1 to 4 carbon atoms or cyano, preferably hydrogen or in particular methyl;

R$^{11}$ is hydrogen, carboxy, sulfo, sulfoalkyl having an alkylene radical of from 1 to 4 carbon atoms, such as sulfomethyl, cyano or carbamoyl, preferably hydrogen, cyano, sulfomethyl, carbamoyl or carboxy;

B$^3$ is hydrogen or alkyl of from 1 to 6 carbon atoms, preferably of from 1 to 4 carbon atoms, which may be substituted by phenyl, sulfo, sulfophenyl or —SO$_2$—Y$^1$, where Y$^1$ is as defined above, but preferably is hydrogen, methyl, ethyl or sulfo-, phenyl- or sulfophenyl-substituted alkyl of from 2 to 4 carbon atoms, such as β-sulfoethyl;

B$^4$ is hydrogen, alkyl of from 1 to 4 carbon atoms or alkyl of from 1 to 4 carbon atoms which is substituted by alkoxy of from 1 to 4 carbon atoms, sulfo, carboxy, sulfato, phenyl, sulfophenyl, acetylamino, benzoylamino, cyano or a group of the formula —SO$_2$—Y$^1$, where Y$^1$ is as defined above, or is alkenyl of from 2 to 4 carbon atoms, cyclohexyl, phenyl or phenyl which is substituted by substituents selected from the group consisting of carboxy, sulfo, benzoylamino, acetylamino, —SO$_2$—Y$^1$, where Y$^1$ is as defined above, and chlorine, but preferably is hydrogen, methyl, ethyl or sulfo-, phenyl- or sulfophenyl-substituted alkyl of from 2 to 4 carbon atoms;

k is zero or 1 (if zero, this group being hydrogen);
m is 1 or 2;
m$_1$ is 1, 2 or 3;

D* is a group of the formula (2), (2a) or (2b) or is phenyl which may be substituted by 1, 2 or 3, preferably 1 or 2, substituents selected from the group consisting of alkyl of from 1 to 4 carbon atoms, alkoxy of from 1 to 4 carbon atoms, chlorine, bromine, hydroxy, carboxy, sulfo, carbamoyl, sulfamoyl and alkanoylamino of from 2 to 5 carbon atoms, preferably methyl, methoxy, ethoxy, chlorine, sulfo, carboxy or hydroxy, and/or by a group of the formula —SO$_2$—Y$^1$, where Y$^1$ is as defined above, one of these substituents being preferably a sulfo or carboxy group and the group —SO$_2$—Y$^1$ being preferably meta or para to the azo group, or D* is naphthyl which is substituted by 1, 2 or 3 sulfo groups or by 1 or 2 sulfo groups and 1 or 2 groups of the formula —SO$_2$—Y$^1$, where Y$^1$ is as defined above, or only by one such group —SO$_2$—Y$^1$, it being possible for D and D* to have meanings identical to or different from each other;

K* is a radical of one of the above-mentioned and -defined formulae (3a) to (3m), it being possible for K and K* to have meanings which are identical or different from each other;

M has one of the abovementioned meanings.

The individual variables, including those which may occur twice in one and the same formula, can have meanings identical to or different from each other.

The free bonds which lead to the azo group in the above formulae (3e), (3f), (3g), (3i) and (3n) and the azo groups in formula (3p) and (3q) are disposed ortho to the hydroxy or amino group. Preferably, this hydroxy group is attached in the α-position of the naphthalene radical.

Alkyl groups of from 1 to 4 carbon atoms are preferably ethyl and in particular methyl; alkoxy groups of from 1 to 4 carbon atoms are preferably ethoxy and in particular methoxy; alkanoylamino groups of from 2 to 5 carbon atoms are preferably propionylamino and in particular acetylamino; and carbalkoxy groups of from 2 to 5 carbon atoms are preferably carbomethoxy and carbethoxy.

Of the novel compounds of the formula (1), preferred ones are those where K is a radical of the formulae (3a) to (3q), and particularly preferred ones are those where K is a radical of the formula (3c), (3f), (3h), (3i), (3p) or (3q), in which in turn the individual variables have the following preferred meanings:

B$^1$ is carboxy or methyl;

Q is phenyl which may be substituted by 1 or 2 substituents selected from the following set of substituents: 2 methyl groups, 2 methoxy groups, 1 chlorine or bromine atom, 2 sulfo groups, 1 carboxy group and 1 vinylsulfonyl or β-sulfatoethylsulfonyl group;

R$^5$ is acetylamino, propionylamino or benzoylamino which may be substituted by 1 or 2 substituents selected from the group consisting of chlorine, methyl, methoxy, nitro, sulfo and β-sulfatoethylsulfonyl;

R$^6$ has one of the abovementioned, in particular a preferred, meaning;

R$^7$ is ureido, acetylamino or benzoylamino;

R$^8$ and R$^9$ are each hydrogen;

R* is hydrogen, acetyl or benzoyl;

R" is hydrogen;

m is 2 in the formulae (3p) and (3q), and one of the —SO$_3$M groups is meta to the hydroxy group and the other —SO$_3$M group is meta or para to the amino group.

The present invention also relates to processes for preparing the novel azo compounds of the formula (1), for example by coupling the diazonium compound of an amino compound of the formula (4), (4a) or (4b)

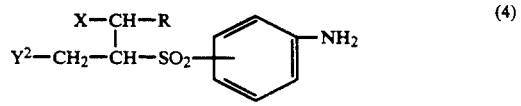

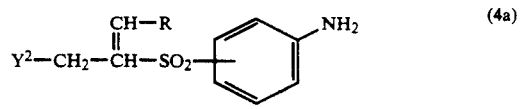

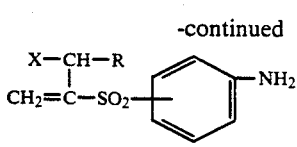

where R, X and $Y^2$ are each as defined above, $Y^2$ being preferably chlorine, bromine, cyano, alkanoyloxy of from 2 to 5 carbon atoms, such as acetyloxy, or sulfato or particularly preferably chlorine, bromine, cyano or acetyloxy, with a coupling component of the formula H-K where K is as defined above; if K, as mentioned above, is a bivalent coupling component, it is possible, if desired, to prepare a disazo compound by reacting this bivalent coupling component with twice the equimolar amount of the diazo component. In the case of a compound of the formula (4), (4a) or (4b) where $Y^2$ is hydroxy, the hydroxy group is converted in the resulting azo compound into a group Y of the novel azo compound (1) as will be indicated later.

The diazotization and coupling reactions are carried out in a conventional and well known manner, for instance the diazotization of the amine (4), (4a) or (4b) in general at a temperature between −5° C. and +15° C. and at a pH below 2 by means of a strong acid and an alkali metal nitrite in a preferably aqueous medium and the coupling reaction in general at a temperature between 0° C. and 35° C. and at a pH between 1.5 and 4.5 in the case of an amino-containing coupling component and at a pH between 3 and 7.5 in the case of a hydroxy-containing coupling component, preferably in an aqueous medium. If the coupling component is a bivalent, doubly couplable compound, containing for example a couplable amino group and also a couplable hydroxy group, then to prepare a disazo compound a coupling with the first mole of the diazonium compound of the amine can take place at an acid pH to form the monoazo compound and the second coupling reaction with the second mole of the diazonium compound of the amine can then be carried out in the weakly acid to weakly alkaline range. This procedure applies for example to the compounds conforming to the general formulae (3p) and (3q), for instance by coupling the aminonaphthol-sulfonic acid first with the first mole of the diazonium compound of the amine of the formula (4), (4a) or (4b) or another aromatic amine conforming to the formula D*—NH$_2$ where D* has the abovementioned meaning other than D, in an acid medium, and then by coupling the resulting monoazo compound with the second mole of a diazonium compound of an amino D*—NH$_2$ where D* has the abovementioned meaning, in a weakly acid, neutral or weakly alkaline range, it being imperative for D* to have one of the meanings indicated for D if the first coupling reaction was not carried out with a diazonium compound of an amine (4), (4a) or (4b); more particularly, the first coupling reaction is initially carried out at a pH between about 0.5 and 2.5 and the second coupling reaction at a pH between 4 and 6.5. If the diazonium compounds are identical in the two coupling reactions, i.e. those of the amino compound (4), (4a) or (4b), the first and second coupling reaction can be carried out in one and the same batch initially in the acid range and then in the weakly acid to weakly alkaline range. To prepare a disazo compound conforming to the formula (3r), the reaction of the coupling component (resorcinol) with the diazonium compound(s) is advantageously carried out initially at a pH between 0.8 and 2 and then at a pH between 6 and 7.5.

Disazo compounds conforming to the formula (1) whose radical K corresponds to the radical of an azo compound which has been assembled from a couplable diazo component and a coupling component, for example a radical conforming to the formula (3s) or (3t), can also be prepared according to the invention by initially coupling the diazonium compound of an amine (4), (4a) or (4b) with the amino-containing and thus diazotizable coupling component, for example in the formulae (3s) and (3t) the aniline- or sulfo-aminonaphthalene components substituted by the substituents $R^6$ and $R^7$, and, in the resulting amino-azo compound, diazotizing the amino group and coupling it with a coupling component, for example the coupling component H-K*, to form the disazo compound.

These possible ways of synthesizing disazo compounds are all similar to those described in the literature or to methods for synthesizing disazo compounds familiar to the person skilled in the art.

Coupling components which can be used for preparing the dyes according to the invention and which conform for example to the formulae (3a) to (3n) are for example: 1,3-diaminobenzene-5-sulfonic acid, phenol, cresol, resorcinol, 2-ethoxyphenol, 4-methylphenol, 3-sulfophenol, salicylic acid, 3-sulfo-1-naphthol, 4-sulfo-1-naphthol, 5-sulfo-1-naphthol, 3,6-disulfo-8-naphthol, 4,6-disulfo-8-naphthol, 1-naphthol-3,8-disulfonic acid, 1-amino-8-naphthol-4-sulfonic acid, 1-amino-8-naphthol-5-sulfonic acid, 1-amino-8-naphthol-2,4-disulfonic acid, 2-amino-5-naphthol-7-sulfonic acid, 2-amino-5-naphthol-1,7-disulfonic acid, 1-amino-5-naphthol-7-sulfonic acid, 2-amino-8-naphthol-6-sulfonic acid, 2-amino-8-naphthol-3,6-disulfonic acid, 2-amino-8-naphthol-4,6-disulfonic acid, 1-amino-8-naphthol-3,6- or -4,6-disulfonic acid, 1-acryloylamino-8-naphthol-3,6- or -4,6-disulfonic acid, 1-propionylamino-8-naphthol-3,6- or -4,6-disulfonic acid, 1-acetylamino-8-naphthol-4-sulfonic acid, 1-acetylamino-8-naphthol-3,6- or -4,6-disulfonic acid, 1-benzoylamino-8-naphthol-3,6-or -4,6-disulfonic acid, 2-naphthol-5,7-disulfonic acid, 2-naphthol-3,6- and -6,8-disulfonic acid, 1,8-dihydroxynaphthalene-3,6-disulfonic acid, 1,8-dihydroxynaphthalene-6-sulfonic acid, 1-naphthol-3,6,8-trisulfonic acid, 2-acetylamino-5-naphthol-7-sulfonic acid, 2-benzoylamino-8-naphthol-6-sulfonic acid, 2-(p'-tosylamino)-5-naphthol-7-sulfonic acid, 2-acetylamino-8-naphthol-3,6-disulfonic acid, 2-acetylamino-5-naphthol-1,7-disulfonic acid, 3-benzoylamino-8-naphthol-6-sulfonic acid, 2-phenylsulfonylamino-5-naphthol-7-sulfonic acid, 2-(N-methyl-N-acetyl)amino-8-naphthol-6-sulfonic acid, N-ethyl-N-benzylaniline-3-sulfonic acid, N,N-bis($\beta$-hydroxyethyl)aniline, N,N-bis($\beta$-sulfatoethyl)aniline, N,N-bis($\beta$-hydroxyethyl)-2-methoxy-5-chloroaniline, N-($\beta$-sulfatoethyl)-2,5-dimethoxyaniline, N-($\beta$-sulfatoethyl)-2-chloroaniline, acetoacetyl-2-naphthylamide-5-sulfonic acid, N-acetoacetylaniline-3- or -4-sulfonicacid,N-acetoacetyl-2-methoxy-5-sulfoaniline, N-acetoacetyl-4-methoxy-3-sulfoaniline, N-acetoacetyl-2-methoxy-5-methyl-4-sulfoaniline, N-acetoacetyl-2,5-dimethoxy-4-sulfoaniline, N-acetoacetyl-2-methoxy-5-methyl-4-($\beta$-sulfatoethylsulfonyl)aniline, N-acetoacetyl-2,5-dimethoxy-4-($\beta$-sulfatoethylsulfonyl)aniline, N-acetoacetyl-2-methoxy-5-($\beta$-sulfatoethylsulfonyl)aniline, N-acetoacetyl-4-($\beta$-sulfatoethylsulfonyl)aniline, N-acetoacetyl-3-($\beta$-sulfatoethylsulfonyl)aniline, 1-(4'-$\beta$-sulfatoethylsulfonylphenyl)-3-methyl-5-pyrazolone, 1-(4'-β-sulfatosulfonyethylsulfonylphenyl)-3-carboxy-5-pyrazolone, 1-(4'-sulfophenyl)-3-methyl-5-pyrazolone, 1-(4'-sulfophenyl)-3-carboxy-5-pyrazolone, 1-(2'-chloro-5,-sulfophenyl)-3-methyl-or-3-carboxy-5-pyrazolone, 1-(3'-sulfophenyl)-3-carboxy-5-pyrazolone, 1-(2'-methoxy-4'-sulfophenyl)-3-carboxy-5-pyrazolone, 1-(3'-sulfophenyl)-3-methyl-5-aminopyrazole, 1-(4'-sulfophenyl)-3-methyl-5-aminopyrazole, 1-(2'-methoxy-5'-sulfophenyl)-3-methyl-5-aminopyrazole, 1-(2'-methoxy-5'-methyl-4'-sulfophenyl)-3-methyl-5-aminopyrazole, 1-(2'-chloro-5'-sulfophenyl)-3-methyl-5-aminopyrazole, 1-(3'-amino-4'-sulfophenyl)-3-carbethoxy-5-pyrazolone, 1-(4'-β-sulfatoethylsulfonylphenyl)-3-carbethoxy-5-pyrazolone, 1-(3'-amino-6'-methylphenyl)-3-carboxy-5-pyrazolone, 2-N-methylamino-8-naphthol-6-sulfonic acid, 3-carboxy-5-pyrazolone, 1-phenyl-3-carboxy-5-pyrazolone, 1-(4'-nitrophenyl)-3-carboxy-5-pyrazolone, 1-(3'-acetylaminophenyl)-3-carboxy-5-pyrazolone, 1-(3'-carboxyphenyl)-3-methyl-5-pyrazolone, 2-hydroxy-3-carboxynaphthalene, 2-hydroxy-6-carboxynaphthalene, 8-hydroxyquinoline-5-sulfonic acid, 1,4-dimethyl-2-hydroxy-6-pyridone-5-sulfonic acid, N-sulfomethylaniline, 3-acetylamino-5-naphthol-7-sulfonic acid, 2-methylamino-8-naphthol-6-sulfonic acid, 1-(β-hydroxyethyl)-4-methyl-6-hydroxy-2-pyridone, 1-(β-hydroxyethyl)-3-cyano-4-methyl-6-hydroxy-2-pyridone, 1-(β-hydroxyethyl)-3-carbamoyl-4-methyl-6-hydroxy-2-pyridone, 1-(β-hydroxyethyl)-4-methyl-6-hydroxy-2-pyridone-3-sulfonic acid, 1-(β-sulfatoethyl)-4-methyl-6-hydroxy-2-pyridone, 1-(β-sulfatoethyl)-3-cyano-4-methyl-6-hydroxy-2-pyridone, 1-(β-sulfatoethyl)-3-carbamoyl-4-methyl-6-hydroxy-2-pyridone, 1-(β-sulfatoethyl)-4-methyl-6-hydroxy-2-pyridone-3-sulfonic acid, 1-(β-sulfatoethyl)-4-methyl-6-hydroxy-2-pyridone, 1-(β-sulfatoethyl)-3-carbamoyl-4-methyl-6-hydroxy-2-pyridone, 1-(β-sulfatoethyl)-4-methyl-6-hydroxy-2-pyridone-3-sulfonic acid, 1-carboxymethyl-4-methyl-6-hydroxy-2-pyridone, 1-carboxymethyl-3-cyano-4-methyl-6-hydroxy-2-pyridone, 1-carboxymethyl-3-carbamoyl-4-methyl-6-hydroxy-2-pyridone, 1-carboxymethyl-4-methyl-6-hydroxy-2-pyridone-3-sulfonic acid, 1-(β-carboxyethyl)-4-methyl-6-hydroxy-2-pyridone, 1-(β-carboxyethyl)-3-cyano-4-methyl-6-hydroxy-2-pyridone, 1-(β-carboxyethyl)-3-carbamoyl-4-methyl-6-hydroxy-2-pyridone, 1-(β-carboxyethyl)-4-methyl-6-hydroxy-2-pyridone-2-sulfonic acid, 1-(β-acetylaminoethyl)-4-methyl-6-hydroxy-2-pyridone, 1-(β-acetylaminoethyl)-3-cyano-4-methyl-6-hydroxy-2-pyridone, 1-(β-acetylaminoethyl)-3-carbamoyl-4-methyl-6-hydroxy-2-pyridone, 1-(β-acetylaminoethyl)-4-methyl-6-hydroxy-2-pyridone-3-sulfonic acid, 1-(β-acetylaminopropyl)-4-methyl-6-hydroxy-2-pyridone, 1-(β-acetylaminopropyl)-3-cyano-4-methyl-6-hydroxy-2-pyridone, 1-(β-acetylaminopropyl)-3-carbamoyl-4-methyl-6-hydroxy-2-pyridone, 1-(β-acetylaminopropyl)-4-methyl-6-hydroxy-2-pyridone-3-sulfonic acid, 4-hydroxy-2-quinoline, 1-amino-8-hydroxy-2-(phenylazo)naphthalene-3,6-disulfonic acid, 1-amino-8-hydroxy-2-(4'-sulfophenylazo)naphthalene-3,6-disulfonic acid, 1-amino-8-hydroxy-2-(2',5'disulfophenylazo)naphthalene-3,6-disulfonic acid, 1(β-aminoethyl)-3-cyano-4-methyl-6-hydroxy-2-pyridone, 1-(γ-aminopropyl)-3-sulfomethyl-4-methyl-6-hydroxy-2-pyridone, 1,3-diaminobenzene, 1-amino-3-(N,N-di-β-hydroxyethylamino)benzene, 1-amino-3-(N,N-di-β-sulfatoethylamino)benzene, 1-amino-3-(N,N-di-β-hydroxyethylamino)-4-methoxybenzene, 1-amino-3-(N,N-di-β-sulfatoethylamino)-4-methoxybenzene, 1-amino-3-(sulfobenzylamino)benzene, 1-amino-3-(sulfobenzylamino)-4-chlorobenzene, 1-amino-3-(N,N-disulfobenzylamino)-benzene, 1-hydroxy-3- or -4-methylbenzene, 1-hydroxybenzene-4-sulfonic acid, 1-hydroxynaphthalene, 2-hydroxynaphthalene, 2-hydroxynaphthalene-6- or -7-sulfonic acid, 1-hydroxynaphthalene-4,7-disulfonic acid, 1-amino-3-methylbenzene, 1-amino-2-methoxy-5-methylbenzene, 1-amino-2,5-dimethylbenzene, 3-aminophenylurea, 1-amino-3-acetylaminobenzene, 1-amino-3-(hydroxyacetylamino)benzene, 1,3-diaminobenzene-4-sulfonic acid, 1-aminonaphthalene-6- or -8-sulfonic acid, 1-amino-2-methoxynaphthalene-6-sulfonic acid, 2-aminonaphthalene-5,7-disulfonic acid, 1-amino-8-hydroxynaphthalene-6-sulfonic acid, 2-hydroxy-3-aminonaphthalene-5,7-disulfonic acid, 1-amino-8-hydroxynaphthalene-2,4,6-trisulfonic acid, 1-hydroxy-8-acetylaminonaphthalene-3-sulfonic acid, 1-benzoylamino-8-hydroxynaphthalene-3,6- or -4,6-disulfonic acid, 2-benzoylamino-5-hydroxynaphthalene-7-sulfonic acid, 2-methyl- and 2-ethylamino-5-hydroxynaphthalene-7-sulfonic acid, 2-(N-acetyl-N-methylamino)-5-hydroxynaphthalene-7-sulfonic acid, 2-ethylamino-8-hydroxynaphthalene-6-sulfonic acid,2-acetylamino-8-hydroxynaphthalene-6-sulfonic acid, 1-(4'-aminobenzoylamino)-8-hydroxynaphthalene-3,6- and -4,6-disulfonic acid, 1-(4'-nitrobenzoylamino)-8-hydroxynaphthalene-3,6- and -4,6-disulfonic acid, 1-(3'-aminobenzoylamino)-6-hydroxynaphthalene-3,6- and -4,6-disulfonic acid, 1-(3'-nitrobenzoylamino)-8-hydroxynaphthalene-3,6- and -4,6-disulfonic acid, 2-(4'-amino-3'-sulfophenyl)amino-5-hydroxynaphthalene-7-sulfonic acid, 3-methyl-5-pyrazolone, 1-phenyl-3-methyl-5-pyrazolone, 1-(3'-aminophenyl)-3-methyl-5-pyrazolone, 1-(2',5'-disulfophenyl)-3-methyl-5-pyrazolon e, 1-(2'-methyl-4'-sulfophenyl)-5-pyrazolone-3-carboxylic acid, 1-(4',8'-disulfonaphthyl-2'-yl)-3-methyl-5-pyrazolone, 1-(5',7'-disulfo-2-naphthyl)-3-methyl-5-pyrazolone, 1-(2',5'-dichloro-4'-sulfophenyl)-3-methyl-5-pyrazolone, 3-aminocarbonyl-4-methyl-6-hydroxy-2-pyridone, 1-ethyl-3-cyano-or -3-chloro-4-methyl-6-hydroxy-2-pyridone, 1-ethyl-3-sulfomethyl-4-methyl-6-hydroxy-2-pyridone, 2,4,6-triamino-3-cyanopyridine, 2-(3'-sulfophenyl)amino-4,6-diamino-3-cyanopyridine, 2-(2'-hydroxyethylamino)-3-cyano-4-methyl-6-aminopyridine, 2,6-bis(2'-hydroxyethylamino)-3-cyano-4-methylpyridine, 1-ethyl-3-carbamoyl-4-methyl-6-hydroxy-2-pyridone, 1-ethyl-3-sulfomethyl-4-methyl-5-carbamoyl-6-hydroxy-2-pyridone, N-acetoacetylaminobenzene, 5-acetylamino-2-sulfoaniline.

The compounds of the formulae (4), (4a) and (4b) which are usable according to the invention for synthesizing the azo compounds (1) according to the invention have not been described before. The invention thus also relates to these compounds, processes for preparing them and their use for synthesizing dyes, in particular the azo compounds (1) according to the invention. They can be prepared according to the invention by oxidizing a compound of the formula (5)

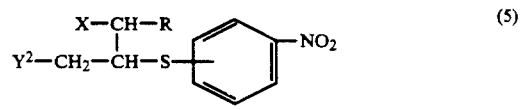
(5)

where $Y^2$, X and R are each as defined above, $Y^2$ being preferably chlorine, bromine, alkanoyloxy of from 2 to 5 carbon atoms, such as acetyloxy, or cyano, to form sulfonyl compounds, the oxidizing agent used being for example potassium permanganate, sodium perhydrogensulfate, potassium perhydrogensulfate, organic peracids, for example peroxyacetic acid, sodium peroxide, hydrogen peroxide and chlorine in aqueous solution. The oxidation reaction can take place at a temperature of between 10° C. and 100° C., preferably between 50° C. and 90° C. The oxidation of the compounds of formula (5) to form the corresponding sulfonyl compound of the hereinafter indicated formula (6) is preferably carried out in an aqueous-organic or purely organic medium, using as organic solvents those which are soluble in water and miscible with water and inert to the oxidizing agents. Such organic solvents are for example glacial acetic acid and dioxane. Preference is given to using glacial acetic acid, in particular in a mixture with water. For example, the oxidation reaction can be carried out by means of hydrogen peroxide in anhydrous acetic acid or in water-containing acetic acid having a water content of up to 20% by weight at a temperature between 30° C. and 100° C., preferably between 60° C. and 90° C. The hydrogen peroxide content is in general between 10 and 35% by weight, preferably between 20 and 35% by weight.

The thus obtainable compounds of the formula (6)

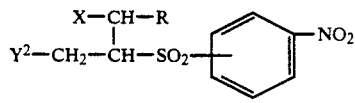
(6)

where $Y^2$, R and X are each as defined above, can be reduced to a novel aniline compound of the formula (4), for example by catalytic reduction by means of hydrogen in the presence of a customary noble metal catalyst or in an acid, aqueous-organic medium by means of non-noble metals, such as iron or zinc, the aqueous acid medium used being preferably aqueous hydrochloric acid. Preferably, the reduction is carried out in an aqeuous, acid medium or in anhydrous organic solvents, for example glacial acetic acid, by means of palladium/activated carbon, at a temperature between 10° C. and 100° C., preferably between 20° C. and 50° C.

The compounds of the formulae (5) and (6) are likewise new. The invention thus also relates to these compounds, processes for preparing them and their use as intermediates for synthesizing azo compounds. The compounds of the formulae (4), (5) and (6) can be summarized under the formula (7)

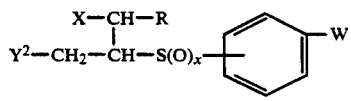
(7)

where $Y^2$, X and R are each as defined above, x is zero or 2 and W is nitro or amino.

The starting compounds of the formula (5) can be prepared according to the invention by adding a nitrobenzenesulfenyl halide, preferably as sulfenyl chloride, to a compound of the formula (8)

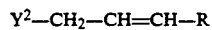
$Y^2$—CH$_2$—CH=CH—R (8)

where $Y^2$ and R are each as defined above. The reaction is carried out for example as described in J. Org. Chem. 49, 1314 (1984) and J. Chem. Soc. 1968, 1339. More particularly, the reaction according to the invention takes place in inert organic solvents, for example dichloromethane, carbon tetrachloride, chlorobenzene or the dichlorobenzenes, at a temperature between −50° C. and 0° C., preferably between −40° C. and −25° C.

The nitrophenylsulfenyl halide starting compounds themselves can be prepared in analogy with known procedures (see for example Liebigs Ann. 400, 2 (1913)) by starting from the nitrobenzene-thiol or -thiolate or a bis(nitrophenyl) disulfide and reacting it in an inert solvent, for example dichloromethane, chloroform, carbon tetrachloride, chlorobenzene or a dichlorobenzene or an isomeric dichlorobenzene mixture, preferably in dichloromethane, chloroform, chlorobenzene or dichlorobenzene, at a temperature between −80° C. and +20° C., preferably between −50° C. and −20° C., with a halogenating agent. Such halogenating agents are preferably chlorine, bromine, N-chlorosuccinimide and N-bromosuccinimide. The nitrophenyl isopropyl sulfone compound conforming to the formula (6) where $Y^2$ is as defined above, preferably being a halogen atom, such as bromine or in particular chlorine, cyano or an alkanoyloxy group of from 2 to 5 carbon atoms, such as acetyloxy, can also be prepared in a simple manner by reacting thiophenol with chlorine to give phenylsulfenyl chloride and adding the latter to an olefin compound of the above-mentioned and -defined formula (8) to form the compound of the formula (9)

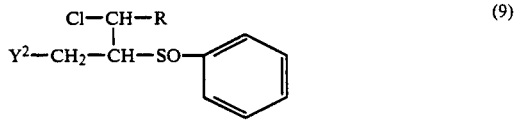
(9)

where R and $Y^2$ are each as defined above, then oxidizing this compound of the formula (9) by means of hydrogen peroxide to give the compound of the formula (10)

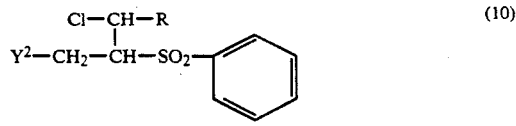
(10)

where R and $Y^2$ are each as defined above, and then nitrating this compound by analogy with known procedures for nitrating benzene compounds to form a meta-nitrobenzeneisopropylsulfonyl compound conforming to the formula (6). Here the reaction of the thiophenol with chlorine takes place at a temperature between −20° C. and +20° C., preferably between −10° C. and +10° C., in an organic solvent which is inert toward the reactants, preferably a halogen-substituted hydrocarbon, for example dichloromethane or chlorobenzene. Without isolating the resulting phenylsulfenyl chloride it can be reacted in the same batch with the olefin of the formula (8), which reaction is likewise carried out in a solvent which is inert toward the reactants, for example one of the abovementioned solvents, at a temperature between −50° C. and 0° C., preferably between −45° C. and −35° C. After the reaction has ended, the solvent is distilled off and the resulting compound of the formula (9) is either purified or subjected directly to the oxidation process. The latter is likewise carried out in a water miscible organic solvent which is inert toward the reactants, such as an alkanecarboxylic acid, preferably an alkanecarboxylic acid having an alkyl radical of from 1 to 4 carbon atoms, in particular acetic acid, at a temperature between 50° C. and 100° C., preferably between 60° C. and 90° C., by means of hydrogen peroxide, which is used in the reaction in the form of a 10 to 40% by weight, preferably 25 to 35% by weight, aqueous solution, while a customary oxidation catalyst, for example an alkali metal tungstate, is used. After the oxidation batch has cooled down, the resulting compound of the formula (10) can be filtered out of the batch, with or without prior addition of water. Further purification is no longer required. This sulfonyl compound of the formula (10) is then nitrated by means of a nitrating acid, a mixture of concentrated sulfuric acid and nitric acid, preferably with a nitric acid content of about 30% by weight, at a temperature between 30° C. and 70° C., preferably between 40° C. and 50° C.

Not only the compounds conforming to the formula (1) but also those of the formulae (4), (5) and (6) where Y and $Y^2$ are each hydroxyl can be converted in a conventional and known manner into compounds where Y and $Y^2$ each have a meaning other than hydroxy, for example into their ester derivatives, for example of polybasic inorganic acids or of aliphatic and aromatic carboxylic or sulfonic acids, for example into compounds where Y and $Y^2$ are each a chlorine atom or a sulfato, phosphato, acetyloxy or toluylsulfonyloxy group.

Suitable esterifying and acylating agents for this purpose are for example the corresponding inorganic or organic acids or anhydrides, halides or amides thereof, for example sulfuric acid, $SO_3$-containing sulfuric acid, chlorosulfonic acid, amidosulfuric acid, phosphoric acid, phosphoryl chloride, mixtures of phosphoric acid and phosphorus pentoxide, acetic anhydride, toluenesulfonyl chloride and thionyl chloride.

Those compounds which contain a vinyl group can be prepared from their analogous ester derivatives, for example those where $Y^2$ is sulfato or chlorine, by the action of an alkali, for instance in an aqueous medium at a pH of from 8 to 10 and at a temperature between 20° C. and 50° C. in the course of 10 to 20 minutes. In this reaction, the action of the alkali can eliminate not only the group $Y^2$ but also, alternatively thereto, the group X together with a hydrogen atom to form an olefinic bond. This converts the compound (1) containing a radical (2) into compounds containing a radical (2a) or (2b) or the compounds of the formula (4) into compounds of the formula (4a) or (4b) and the compounds of the formulae (5) and (6) into compounds conforming respectively on the one hand to the formula (5a) and (5b) and on the other (6a) and (6b)

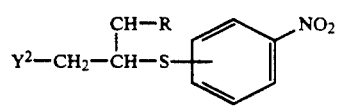
(5a)

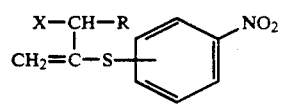
(5b)

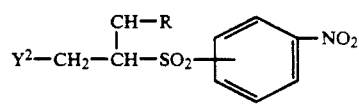
(6a)

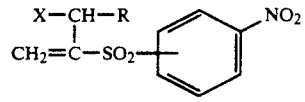
(6b)

where X, R and $Y^2$ are each as defined above. These compounds of the formulae (5a), (5b), (6a) and (6b) are likewise new; they can be summarized under the formulae (7a) and (7b)

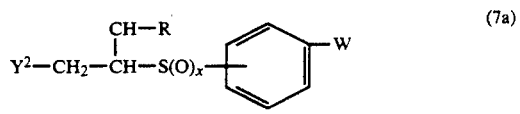
(7a)

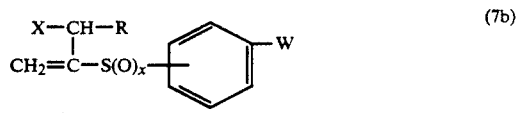
(7b)

where $Y^2$, X, R, W and x are each as defined above. The present invention accordingly also relates to these compounds, processes for preparing them and their use as intermediates for synthesizing azo compounds.

Compounds of the formulae (1), (4), (5) and (6) where Y and $Y^2$ are each trialkylammonium or thiosulfato can be prepared by analogy with known procedures from their vinyl derivatives (conforming to the formulae (2a), (2b), (7a) and (7b)) by reaction with the corresponding trialkylamine or with an alkali metal salt of thiosulfuric acid, such as sodium thiosulfate.

The separation and isolation of the compounds (1) from the aqueous synthesis solutions can be effected by generally known methods for water soluble compounds, for example by precipitating from the reaction medium by means of an electrolyte, for example sodium chloride or potassium chloride, or else by evaporating the reaction solution, for example by spray drying. If the latter manner of isolation is chosen, it is frequently advisable to separate off any sulfate present in these solutions prior to evaporation by precipitation as calcium sulfate and removal by filtration.

The novel compounds of the formula (1)—hereinafter referred to as compounds (1)—have fiber reactive properties and possess very useful dye properties. They can therefore be used for dyeing (including printing) hydroxy-containing and/or carboxamido-containing materials. Moreover, the solutions obtained in the synthesis of the compounds (1) can be used directly in dyeing as a liquid preparation with or without the addition of a buffer substance and with or without prior concentrating.

The present invention therefore also provides for the use of the compounds (1) for dyeing (including printing) hydroxy- and/or carboxamido-containing materials as well as for processes for the application thereof to these substrates. Preference is given to employing the materials in the form of fiber materials, in particular in the form of textile fibers, such as hanks, packages and fabrics. Methods analogous to known methods can be employed.

Hydroxy-containing materials are those of natural or synthetic origin, for example cellulose fiber materials or regenerated products thereof and polyvinyl alcohols. Cellulose fiber materials are preferably cotton but other vegetable fibers as well, such as linen, hemp, jute and ramie fibers; regenerated cellulose fibers are for example staple viscose and filament viscose.

Carboxamido-containing materials are for example synthetic and natural polyamides and polyurethanes in the form of fibers, for example wool and other animal hairs, silk, leather, nylon-6.6, nylon-6, nylon-11 and nylon-4.

The compounds (1), as provided for by the use according to the present invention, can be applied to or fixed on the substrates mentioned, in particular on the fiber materials mentioned, by the application techniques known for water soluble, fiber reactive dyes, for example by applying the compound (1) to the substrate in dissolved form or introducing it therein and fixing it thereon by the action of heat or by the action of an alkaline agent or both. Such dyeing and fixing techniques have been numerously described in the literature (for example in European Patent Application Publication No. 0 181 585 A2).

A particular advantage of the compounds (1) is that, in customary dyeing processes, even if electrolytes and alkaline compounds are used in distinctly reduced amounts than is customary, they surprisingly produce dyeings having higher color yields than are obtained with the customary amounts of salt. For in general the present state of the art still requires high levels of electrolytes in the dyeing liquor to produce intensive dyeings with fiber reactive dyes. Such high salt levels, which in general are above 50 g per liter of dyeing liquor, are undesirable for ecological reasons. However, the compounds (1) make it possible to use dyeing liquors in which the levels of added electrolyte are below 40 g per liter of dyeing liquor, preferably only between 10 and 35 g per liter of dyeing liquor.

The dyeings obtainable according to the invention have good light fastness properties, in particular on cellulose fiber materials, not only in the dry state of the dyeing but also in the wet state, when moistened for example with a perspiration solution, and also good wet fastness properties, for example good wash fastness properties at 60° C. to 95° C., even in the presence of perborates, good acid and alkaline milling, cross-dyeing and perspiration fastness properties, a high steam resistance, good alkali, acid, water and seawater fastness properties, also good pleating, hot press and crock fastness properties. Similarly, they have a high acid fading resistance when moist dyed material still containing acetic acid is stored.

The Examples which follow serve to illustrate the invention. Parts and percentages are by weight, unless otherwise stated. Parts by weight bear the same relation to parts by volume as the kilogram to the liter.

The compounds described in these Examples by means of a formula are indicated in the form of the free acids; in general, they are prepared and isolated in the form of their alkali metal salts, such as lithium, sodium or potassium salts, and used for dyeing in the form of their salts. Similarly, the starting compounds and components mentioned in the form of the free acid in the subsequent Examples, in particular Table Examples, can be used in the synthesis as such or in the form of their salts, preferably alkali metal salts.

The absorption maxima ($\lambda_{max}$ values) indicated for the visible region for the compounds according to the invention were determined on aqueous solutions of the alkali metal salts. In the Table Examples the $\lambda_{max}$ values are given in brackets in the hue column; the wavelength unit is nm.

The $^1$H-NMR data were measured in dimethyl sulfoxide-$d_6$ as solvent using tetramethylsilane as internal standard, unless otherwise stated.

EXAMPLE A

To synthesize 1,3-dichloroisopropyl 4'-nitrophenyl sulfide, chlorine is passed with cooling at −10° C. into a suspension of 100 parts of bis(4-nitrophenyl) disulfide in 1000 parts by volume of dichloromethane until all the disulfide has gone into solution. The batch is then cooled down to −40° C., and 80 parts of allyl chloride are gradually added over about 30 minutes. The batch is then warmed to 20° C. and subsequently stirred at that temperature for about 16 hours more, and volatiles are then removed under reduced pressure.

The residue obtained is recrystallized from diethyl ether. This gives about 122 to 123 parts of the compound of the formula

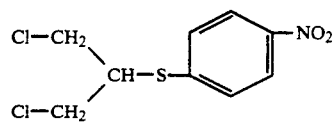

in the form of pale yellow crystals having a melting point of 62° C.

C, H, N analysis:
calculated: C 40.6%, H 3.4%, N 5.2%;
found C 40.4%, H 3.4%, N 5.3%.
$^1$H-NMR analysis: 4.0 ppm (4H;d), 4.22 ppm (1H;quint.), 7.65 ppm (2H;d), 8.18 ppm (2H;d).

EXAMPLE B

To prepare 1,3-dichloroisopropyl 4'-nitrophenyl sulfone, 13.3 parts of 1,3-dichloroisopropyl 4'-nitrophenyl sulfide (Example A; in the form of the crude product or after recrystallization) are dissolved in 100 parts by volume of glacial acetic acid, 0.05 part of sodium tungstate is added, the batch is heated to 80° C., and at that temperature 11 parts by volume of 35% strength aqueous hydrogen peroxide are gradually added with stirring. Stirring is subsequently continued for about 15 minutes longer, and the batch is cooled down to 0° C. The precipitated crystals are filtered off with suction and recrystallized from ethanol. This gives about 11.5 parts of a compound of the formula

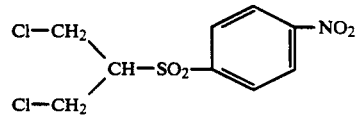

having a melting point of 105° C.
C, H, N analysis:
calculated: C 36.25%, H 3.04%, N 4.7%;
found: C 36.3%, H 3.0%, N 4.8%.
$^1$H-NMR analysis 4.07 ppm (4H;m), 4.5 ppm (1H;m), (in CDCl$_3$): 8.2 ppm (4H;d), 8.45 ppm (4H;d).

EXAMPLE C

To prepare 1,3-dichloroisopropyl 4'-aminophenyl sulfone, first a mixture is prepared from 80 parts of zinc powder, 360 parts of water, 160 parts by volume of dioxane and 10 parts by volume of concentrated aqueous hydrochloric acid. To this mixture is slowly added with thorough stirring at about 20° C. a solution of 48 parts of 1,3-dichloroisopropyl 4'-nitrophenyl sulfone (Example B) in 320 parts by volume of dioxane at the same time as a mixture of 310 parts by volume of concentrated aqueous hydrochloric acid, 160 parts of water and 80 parts by volume of dioxane. Stirring is continued until the zinc is largely consumed and has gone into solution, the precipitate is filtered off and washed with dioxane, and the combined filtrates are adjusted to pH 4 with sodium acetate. The filtrate is subsequently stirred at about 20° C. for about 12 hours, and the resulting white precipitate is filtered off with suction and dried. This gives about 36 parts of a finely crystalline compound of the formula

```
Cl—CH2
       \
        CH—SO2—⟨ ⟩—NH2
       /
Cl—CH2
``` having a melting point of 104° C.

Elemental analysis:
calculated: C 40.3%, H 4.1%, N 5.2%, Cl 26.4%;
found: C 40.8%, H 4.2%, N 5.3%, Cl 25.9%.

$^1$H-NMR analysis: 3.95 ppm (5H;m), 6.25 ppm (2H;br), 6.65 ppm (2H;d), 7.5 ppm (2H;d).

EXAMPLE D

To prepare 1-chloro-3-acetyloxyisopropyl 4'-nitrophenyl sulfide, chlorine is passed at −10° C. into a suspension of 92.4 parts of bis(4-nitrophenyl) disulfide in 500 parts by volume of dichloromethane until a clear solution has formed. Dry nitrogen is then passed in for about 15 minutes, and 108 parts by volume of allyl acetate are then gradually added at a temperature of −40° C. in the course of about 15 minutes. The solution is subsequently stirred for one hour and then cooled down to 70° C., and a pale yellow precipitate is isolated.

This gives 152 parts of a finely crystalline powder of the compound of the formula

```
Cl—CH2
       \
        CH—S—⟨ ⟩—NO2
       /
CH3—CO—O—CH2
``` having a melting point of 110° C.

Elemental analysis:
calculated: C 45.6%, H 4.17%, N 4.8%, Cl 12.2%;
found: C 45.6%, H 4.2%, N 4.8%, Cl 12.4%.

$^1$H-NMR analysis: 2.05 ppm (3H;s), 3.97 ppm (2H;d), 4.18 ppm (1H;quint.), 4.35 ppm (2H;m), 7.67 ppm (2H;d), 8.18 ppm (2H;d).

EXAMPLE E

To prepare 1-chloro-3-acetyloxyisopropyl 4'-nitrophenyl sulfone, a 70° C. solution of 145 parts of 1-chloro-3-acetyloxyisopropyl 4'-nitrophenyl sulfide (Example D) in 450 parts by volume of glacial acetic acid is admixed, following the addition of 2 parts of sodium tungstate, with 120 parts by volume of 35% strength aqueous hydrogen peroxide, added gradually over about 30 minutes. The batch is subsequently stirred for about 15 minutes and then cooled down to about 20° C., 100 parts of water are added, the solution is cooled down to 0° C., and the white precipitate is isolated. This gives 145 parts of a finely crystalline powder of the compound 1-chloro-3-acetyloxyisopropyl 4'-nitrophenyl sulfone having a melting point of 89° C.

Elemental analysis:
calculated: C 41.1%, H 3.7%, N 4.3%, Cl 11.0%;
found: C 41.4%, H 3.6%, N 4.1%, Cl 11.1%.

$^1$H-NMR analysis: 1.83 ppm (3H;s), 3.9–4.17 ppm (2H;m), 4.36 ppm (1H;quint.), 4.48 ppm (2H;m), 8.22 ppm (2H;d), 8.48 ppm (2H;d).

EXAMPLE F

To prepare 1-chloro-3-cyanoisopropyl 4'-nitrophenyl sulfide, a solution of 7.6 parts of 4-nitrophenylsulfenyl chloride is gradually admixed at −20° C. with 4.0 parts of allyl cyanide. The batch is subsequently stirred for 1 hour, and volatiles are then removed under reduced pressure. The brown residue remaining behind gradually solidifies. Recrystallization from a mixture of equal parts of diethyl ether and dichloromethane gives 6.7 parts of the compound of the formula

```
Cl—CH2
       \
        CH—S—⟨ ⟩—NO2
       /
NC—CH2
``` in the form of yellowish crystals having a melting point of 68° C.

Elemental analysis:
calculated: C 46.7%, H 3.5%, N 10.9%, Cl 13.8%;
found: C 45.9%, H 3.5%, N 10.9%, Cl 14.6%.

$^1$H-NMR analysis: 3.1 ppm (2H;m), 3.9 ppm (2H;m), 4.27 ppm (1H;m), 7.75 ppm (2H;d), 8.2 ppm (2H;d).

EXAMPLE G

To prepare 1-chloro-3-cyanoisopropyl 4'-nitrophenyl sulfone, a 60° C. solution of 3.84 parts of 1-chloro-3-cyanoisopropyl 4'-nitrophenyl sulfide (Example F) in 30 parts by volume of glacial acetic acid is admixed, following the addition of 0.005 part of sodium tungstate, with 7 parts by volume of a 35% strength aqueous hydrogen peroxide solution, added gradually over a period of 30 minutes. The batch is subsequently stirred for a short time and then cooled down to −15° C., and the precipitated product is isolated after some time.

This gives 2.6 parts of a compound of the formula

```
Cl—CH2
       \
        CH—SO2—⟨ ⟩—NO2
       /
NC—CH2
``` in the form of a white powder having a melting point of 101° C.

Elemental analysis:
calculated: C 41.6%, H 3.1%, N 9.7%, Cl 12.2%;
found: C 41.4%, H 3.0%, N 9.7%, Cl 12.4%.

$^1$H-NMR analysis: 3.2 ppm (2H;m), 4.0 ppm (2H;m), 4.5 ppm (1H;quint.), 8.25 ppm (2H;d), 8.5 ppm (2H;d).

EXAMPLE H

To prepare 1,3-dichloroisopropyl 3'-nitrophenyl sulfide, chlorine is passed into a solution of 55.45 parts of bis(3-nitrophenyl) disulfide in 300 parts by volume of methylene chloride at −10° C., and the batch is subsequently stirred at this temperature for some time longer. Then dry nitrogen is passed through the reaction solution for about 15 minutes, and subsequently 37 parts by volume of allyl chloride are gradually added at −40° C. Stirring is continued for a short time, and volatiles are then removed under reduced pressure. This leaves a brown oil which can be used for preparing the corresponding sulfonyl compound (see Example J) without further purification.

A small amount of the crude sulfide obtained was purified by chromatography. It gave the following $^1$H-NMR analysis values: 4.1 ppm (4H;m), 4.5 ppm (1H;quint.), 7.98 ppm (1H;t), 8.38 ppm (1H; d), 8.61 ppm (1H;d), 8.6 ppm (1H;d).

EXAMPLE J

To prepare 1,3-dichloroisopropyl 3'-nitrophenyl sulfone, a 70° C. solution of the sulfide compound of Example H is admixed, following addition of 0.02 part of sodium tungstate, with 80 parts by volume of a 35% strength aqueous hydrogen peroxide solution, added gradually, the batch is subsequently stirred at 70° C. for about a further 90 minutes, and then a further 20 parts by volume of the hydrogen peroxide solution are added. After further brief stirring, the batch is admixed with 100 parts of water, and cooled down to 0° C., and a finely crystalline precipitate is isolated after some time.

This gives 79.5 parts of the compound of the formula

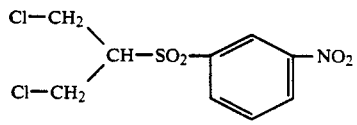

having a melting point of 110° C.

Elemental analysis:
calculated C 36.2%, H 3.04%, N 4.7%, Cl 23.8%, S 10.7%, O 21.4%;
found: C 36.6%, H 3.1%, N 4.7%, Cl 23.5%, S 10.6%, O 21.9%.

$^1$H-NMR analysis: 4.05 ppm (4H;m), 4.5 ppm (1H;t), 7.98 ppm (1H;m), 8.38 ppm (1H;m), 8.61 ppm (1H;m).

EXAMPLE K

To prepare 1-chloro-3-acetyloxyisoprop-yl 4'-aminophenyl sulfone, a mixture of 47 parts of water, 20 parts by volume of dioxane and 15 parts of zinc powder is admixed at 15° C. to 20° C. with a solution of 6 parts of 1-chloro-3-acetyloxyisopropyl 4'-nitrophenyl sulfone (Example C) in 47 parts by volume of dioxane and a mixture of 47 parts by volume of concentrated hydrochloric acid, 20 parts of water and 14 parts by volume of dioxane, both added gradually at the same time with thorough stirring. The batch is subsequently stirred at 15° C. to 20° C. for a further 15 minutes, the precipitate is filtered off, the filtrate is adjusted to pH 4 with sodium acetate, and the precipitated product is isolated after some time. This gives 5 parts of the compound 1-chloro-3-acetyloxyisopropyl 4'-aminophenyl sulfone as a fine white crystalline powder having a melting point of 124° C.

Elemental analysis
calculated: C 45.3%, H 4.4%, N 4.8%, Cl 12.15%;
found: C 45.0%, H 4.75%, N 4.8%, Cl 12.4%.

$^1$H-NMR analysis: 1.90 ppm (3H;s), 3.82 ppm (2H;m), 3.98 ppm (1H;m), 4.38 ppm (2H;m), 6.2 ppm (2H;br), 6.65 ppm (2H;d), 7.45 ppm (2H;d).

EXAMPLE L

To prepare 1-bromo-3-chloroisopropyl 4'-nitrophenyl sulfide, chlorine is passed at −10° C. into a solution of 31 parts of bis(4-nitrophenyl) disulfide in 150 parts by volume of dichloromethane. The batch is subsequently stirred for some time and then dry nitrogen is passed through it for about 15 minutes, followed by the gradual addition at −40° C. of 40 parts of allyl bromide. This is followed by another hour's stirring, heating of the solution to about 20° C. and removal of volatiles under reduced pressure. This gives 51 parts of a brown crystalline crude product which can be used for the synthesis of the corresponding sulfonyl compound (see Example M) without further purification.

A small amount of this crude product was recrystallized from a mixture of equal parts of diethyl ether and dichloromethane. It has a melting point of 60° C.; the following analytical values were obtained:

Elemental analysis:
calculated: C 34.8%, H 2.9%, N 4.5%;
found: C 34.9%, H 2.9%, N 4.6%.

$^1$H-NMR analysis: 3.9 ppm (2H;m), 4.02 ppm (2H;m), 4.27 ppm (1H;quint.), 7.77 ppm (2H;d), 8.19 ppm (2H;d).

EXAMPLE M

To prepare 1-bromo-3-chloroisopropyl 4'-nitrophenyl sulfone, a 70° C. solution of 75 parts of 1-bromo-3-chloroisopropyl 4'-nitrophenyl sulfide in 100 parts by volume of glacial acetic acid was admixed, following the addition of 0.5 part of sodium tungstate, with 86 parts by volume of a 35% strength aqueous hydrogen peroxide solution, added gradually. The batch was subsequently stirred for a short time and then cooled down to 0° C., and after about 2 hours the precipitated product was isolated.

This gave 66 parts of the compound of the formula

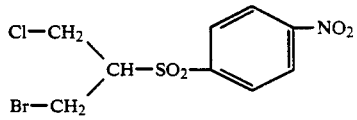

in the form of slightly yellowish crystals having a melting point of 108° C.

C, H, N analysis:
calculated: C 31.5%, H 2.6%, N 4.1%;
found: C 30.7%, H 2.6%, N 3.9%.

$^1$H-NMR analysis: 3.7 ppm (2H;m), 3.93 ppm (2H;m), 4.12 ppm (1H;d), 8.15 ppm (2H;d) 8.43 ppm (2H;d).

EXAMPLE N

To prepare 1,3-dichloroisopropyl 4'-aminophenyl sulfone, 29.8 parts of 1,3-dichloroisopropyl 4'-nitrophenyl sulfone, dissolved in 300 parts by volume of glacial acetic acid, were hydrogenated at a hydrogen pressure of 10 bar in the presence of 1.5 parts of a palladium/active charcoal catalyst (10% of palladium on active charcoal). After the uptake of hydrogen had ceased, the bulk of the acetic acid is distilled off under reduced pressure. The residue is admixed with 10 times the amount of water and filtered with suction, and the filter residue is dried. This leaves the compound of the formula indicated in Example C as a white crystalline powder (24 parts).

EXAMPLE P

To prepare 1,3-dichloroisopropyl 3'-aminophenyl sulfone, 25 parts of 1,3-dichloroisopropyl 3'-nitrophenyl sulfone (Example J), suspended in 300 parts by volume of glacial acetic acid, are hydrogenated in accordance with the directions of Example N. After the uptake of hydrogen has ceased, the bulk of the glacial acetic acid is distilled off, and the residue obtained is stirred into 10 times the amount of water. The reduced product initially precipitates in resinous form, but crystallizes after some time. This gives about 20.8 parts of a white powder of the compound of the formula

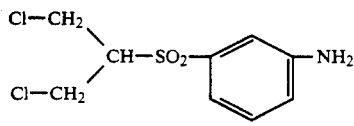

having a melting point of 69° C.

C, H, N analysis:
calculated: C 40.3%, H 4.1%, N 5.2%, Cl 26.4%;
found: C 40.5%, H 4.1%, N 5.2%, Cl 26.3%.

$^1$H-NMR analysis: 4.0 ppm (4H;m), 4.07 ppm (1H;m), 5.65 ppm (2H;br), 6.91 ppm (1H;d) 7.00 ppm (1H;d), 7.09 ppm (1H;t), 7.29 ppm (1H;t).

EXAMPLE Q 76 parts of 4-(1-chloro-3-acetyloxyisopropylsulfonyl)aniline are suspended in 200 parts by volume of concentrated aqueous hydrochloric acid, the batch is heated to 65° C.-70° C., maintained at that temperature for about two hours, then cooled down and brought to a pH between 3 and 3.5 with aqueous sodium hydroxide solution, and the precipitated product is filtered off with suction. This gives 22 parts of a fine white powder of the compound 4-(1-chloro-3-hydroxyisopropylsulfonyl)aniline having a melting point of 88° C.

Elemental analysis:
calculated: C 43.3%, H 2.9%, N 5.6%;
found: C 42.3%, H 4.5%, N 5.8%.

$^1$H-NMR analysis (in CDCl$_3$): 2.7 ppm (1H;t,br), 3.3 ppm (1H;m), 3.8 ppm (2H;n), 4.0–4.2 ppm (2H;m), 4.33 ppm (2H;s,br), 6.75 ppm (1H;d), 7.63 ppm (1H;d).

EXAMPLE R 16.5 parts of 4-(1-chloro-3-hydroxyisopropylsulfonyl)aniline are introduced at 10° C.-20° C. into 50 parts by volume of concentrated sulfuric acid. The mixture is subsequently stirred for a further 2 hours and then poured into 300 parts of ice-water. The precipitated product is filtered off with suction and dried.

This gives 17.5 parts of a white powder of the compound 4-(1-sulfato-3-chloroisopropylsulfonyl)aniline.

Elemental analysis:

calculated: C 32.8%, H 3.66%, N 4.24%;
found: C 32.5%, H 3.6%, N 4.3%.

$^1$H-NMR analysis: 3.75 ppm (1H;m), 3.84 ppm (2H;d) 4.0 ppm (1H;m), 4.1 ppm (1H;m), 6.76 ppm (1H;d), 7.52 ppm (1H;d).

EXAMPLE S 71 parts of chlorine are passed at 0° C. into a solution of 220 parts of thiophenol in 807 parts of dry chlorobenzene under nitrogen in the course of about three hours. Thereafter the batch is stirred for a further 30 minutes. Excess chlorine is then blown out by passing dry nitrogen through the batch. The batch is cooled down to −40° C. 168 parts of allyl chloride are gradually added continuously in the course of about 30 minutes. The batch is subsequently stirred for a further 45 minutes and then warmed to 20° C., and the chlorobenzene is distilled off under reduced pressure.

443 parts of the pale yellow oil obtained are dissolved in 734 parts of acetic acid. 2 parts of sodium tungstate dihydrate are added, the batch is heated to 75° C., and 450 parts of a 35% strength aqueous hydrogen peroxide solution are gradually added continuously in the course of about an hour while a temperature of 80° C. is maintained. The batch is subsequently stirred for about 30 minutes longer, and cooled down to 0° C., and the white precipitate is filtered off with suction, washed three times with about 70 parts water and dried under reduced pressure.

506 parts of the compound obtained, 1,3-dichloroisopropyl phenyl sulfone, are dissolved in 950 parts of 100% strength sulfuric acid; 610 parts of nitrating acid, being 70% sulfuric acid and 30% nitric acid, are gradually added with stirring at 40° C. to 50° C. in the course of about an hour. The batch, which has partly crystallized, is subsequently stirred for about 30 minutes longer and then introduced into 4000 parts of water. The precipitated product is filtered off with suction, washed with 3000 parts of water, ground fine, washed once more with 3000 parts of water, and dried.

The compound obtained, 1,3-dichloroisopropyl 3'-nitrophenyl sulfone, is identical to that of Example J.

EXAMPLE 1

A suspension of 9 parts of 4-(1,3-dichloroisopropylsulfonyl)aniline in a mixture of 40 parts by volume of acetone, 80 parts of water and 16 parts by volume of concentrated aqueous hydrochloric acid are diazotized in a conventional manner by the addition of sodium nitrite. A neutral solution of the sodium salt of 7.9 parts of 1-(4'-sulfophenyl)-3-carboxypyrazol-5-one in 55 parts water is added, and a pH of 4 is set with sodium acetate. After the coupling reaction, carried out in a conventional manner at 15° C. to 20° C., has ended, the resulting azo compound according to the invention is isolated by salting out with sodium chloride and filtration.

Written in the form of the free acid it has the formula

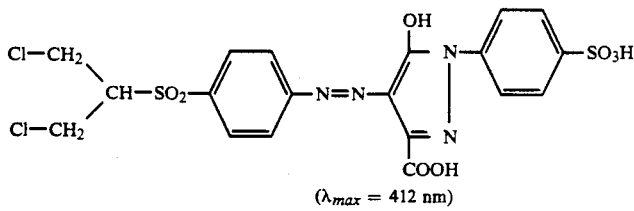

($\lambda_{max}$ = 412 nm)

and shows very good fiber reactive dye properties. Applied by the application and fixing methods known for fiber reactive dyes it produces on the materials mentioned in the description, in particular on cellulose fiber materials, for example cotton, strong yellow dyeings and prints having good fastness properties, of which in particular the light, wet light and perspiration light fastness properties may be singled out.

EXAMPLE 2

9 parts of 4-(1,3-dichloroisopropylsulfonyl)aniline are diazotized in accordance with the directions of Example 1. The diazonium salt solution obtained is admixed with a neutral solution of the sodium salt of 13.5 parts of 2-acetylamino-6-sulfo-8-naphthol in 30 parts of water, the pH is set to 4.5 with sodium acetate, and the coupling reaction is completed at 15° C. to 20° C.

The precipitated novel azo compound of the formula

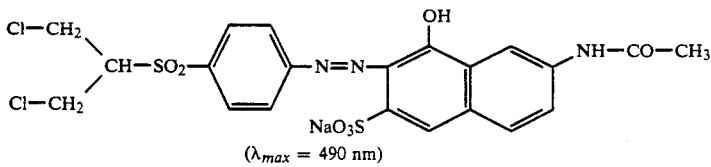

($\lambda_{max}$ = 490 nm)

is filtered off and dried. It has very good fiber reactive dye properties and applied to the materials mentioned in the description, in particular cellulose fiber materials, for example cotton, by the application and fixing methods customary for fiber reactive dyes produces orange dyeings and prints having good fastness properties, of which in particular the light, wet light and perspiration light fastness properties may be singled out.

EXAMPLE 3

10.7 parts of 4-(1',3'-dichloroisopropylsulfonyl)aniline are diazotized in accordance with the directions of Example 1. The diazonium salt solution obtained is admixed with a suspension of 8 parts of 2-sulfo-5-acetylaminoaniline in 50 parts of water, the pH is adjusted to 3 with a 10% strength aqueous sodium carbonate solution, and the coupling reaction is completed initially at 20° C. for 30 minutes and then at 30° C. for 2 hours, pH 3 being maintained with sodium acetate during both periods.

The precipitated novel azo compound of the formula

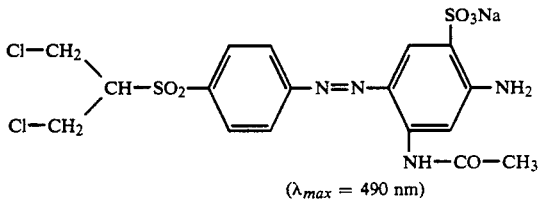

($\lambda_{max}$ = 490 nm)

is filtered off and dried. It has very good fiber reactive dye properties and applied to the materials mentioned in the description, in particular cellulose fiber materials, for example cotton, by the application and fixing methods customary for fiber reactive dyes produces orange dyeings and prints having good fastness properties, of which in particular the light, wet light and perspiration light fastness properties may be singled out.

EXAMPLE 4

8.1 parts of 4-(1'-chloro-3'-acetyloxyisopropylsulfonyl)aniline are suspended in a mixture of 30 parts by volume acetone, 70 parts of water and 16 parts by volume of concentrated aqueous hydrochloric acid and diazotized in accordance with the directions of Example 1. The diazonium salt solution obtained is admixed with a neutral solution of 9.4 parts of 1-(4'-sulfophenyl)-3-carboxypyrazol-5-one in 50 parts of water, and the coupling reaction is carried out at pH 4.5 and at a temperature between 10° C. and 25° C.

The azo compound of the formula (written in the form of the free acid)

($\lambda_{max}$ = 412 nm)

is salted out in the form of the sodium salt with 6 parts of sodium chloride and isolated. It has very good fiber reactive dye properties and applied to the materials mentioned in the description, in particular cellulose fiber materials, for example cotton, by the application and fixing methods customary for fiber reactive dyes produces orange dyeings and prints having good fastness properties, of which in particular the light, wet light and perspiration light fastness properties may be singled out.

quently stirred for about 30 minutes more to complete the coupling reaction. To complete the precipitation of the azo dye according to the invention, 10 parts of sodium chloride are added, and the precipitate is filtered off and dried.

This gives the novel azo compound of the formula (written in the form of the free acid)

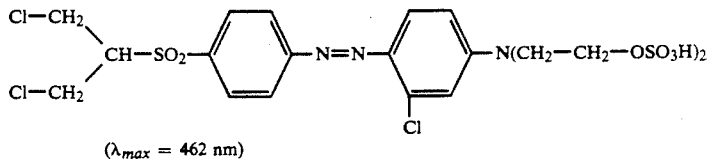

($\lambda_{max}$ = 462 nm)

EXAMPLE 5

A suspension of 9 parts of 3-(1,3-dichloroisopropylsulfonyl)aniline in a mixture of 40 parts by volume of acetone, 80 parts of water and 16 parts by volume of concentrated aqueous hydrochloric acid are diazotized in a conventional manner by the addition of sodium nitrite. The diazonium salt solution obtained is then mixed with a neutral solution of the sodium salt of 13.5 parts of 2-acetylamino-6-sulfo-8-naphthol in 30 parts of water, the pH is set to 4.5 with sodium acetate, and the coupling reaction is completed at 15° C. to 20° C.

The precipitated novel azo compound of the formula as sodium salt in the form of a yellow powder containing only small amounts of an electrolyte salt (sodium chloride). The azo compound according to the invention has very good fiber reactive dye properties. Applied to the materials mentioned in the description, in particular cellulose fiber materials, for example cotton, by the dyeing and printing methods customary for fiber reactive dyes it produces strong yellow dyeings and prints having good fastness properties, of which in particular the light, wet light and perspiration light fast properties may be singled out.

EXAMPLE 7

4 parts of 4-(1,3-dichloroisopropylsulfonyl)aniline are dissolved in 8 parts of concentrated sulfuric acid and diazotized by the gradual addition of a solution of the necessary amount of sodium nitrite in 40 parts of icewa-

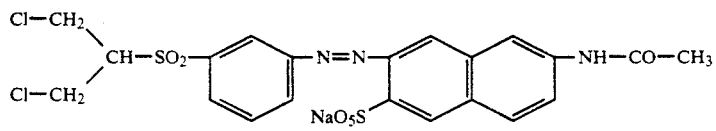

($\lambda_{max}$ = 488 nm)

is filtered off and dried. It has very good fiber reactive dye properties and applied to the materials mentioned in the description, in particular cellulose fiber materials, by the application and fixing methods customary for fiber reactive dyes produces orange dyeings and prints having good fastness properties, of which in particular the light, wet light and perspiration light fastness properties may be singled out.

EXAMPLE 6

A diazonium salt solution of 10.7 parts of 4-(1,3- ter. The diazonium salt solution obtained is clarified by means of kieselguhr and filtration; excess nitrous acid is destroyed in a conventional manner by means of amidosulfuric acid. Then a suspension of 8.4 parts of monoazo compound 2-[4'-($\beta$-sulfatoethylsulfonyl)-phenyl]azo-1-amino-8-hydroxynapthalene-3,6-disulfonic acid as sodium salt in 100 parts of water is added, the batch is set to pH 4.5, and the coupling reaction is completed at about 20° C. and at this pH.

The resulting novel disazo compound, which written in the form of the free acid conforms to the formula

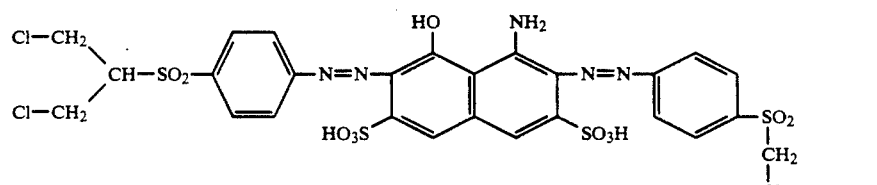

($\lambda_{max}$ = 594 nm)

dichloroisopropylsulfonyl)aniline, prepared similarly to the directions of Example 1, is added to 40 parts by volume of an aqueous solution of 16.8 parts of N,N-bis-($\beta$-sulfatoethyl)-3-chloroaniline. The coupling batch is adjusted to pH 2 with hydrochloric acid and subseis isolated in the form of the sodium salt by salting out with sodium chloride. It has very good fiber reactive dye properties and applied for example to cellulose fiber materials by the application fixing methods customary for fiber reactive dye produces navy dyeings and prints having good fastness properties, of which in particular the light, wet light and perspiration light fastness properties may be singled out.

Written in the form of the free acid it has the formula

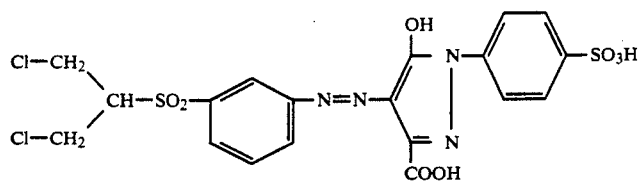

($\lambda_{max}$ = 410 nm)

EXAMPLE 8

26.6 parts of 4-(1,3-dichloroisopropylsulfonyl)aniline are stirred with 40 parts by volume of aqueous concentrated hydrochloric acid to form a homogeneous paste, which is added a little at a time with stirring to a mixture of 5 parts by volume of aqueous 5N sodium nitrite solution in 200 parts of ice-water in the course of an hour. Thereafter a further 15 parts by volume of aqueous 5N sodium nitrite solution are gradually added. The diazonium salt solution obtained is clarified and stirred into a solution at pH 6 of 23.3 parts of 1-($\beta$-sulfoethyl)-4-methyl-6-hydroxy-2-pyridone in 250 parts of water. The coupling reaction is completed at a temperature of about 20° C. and a pH of 6, and the resulting azo compound according to the invention is filtered off with suction and dried.

This gives a yellow dye powder of the sodium salt of the compound of formula

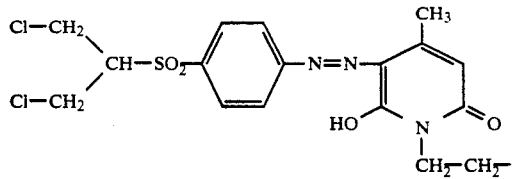

($\lambda_{max}$ = 409 nm)

which has very good fiber reactive dye properties and applied by the application fixing methods customary for fiber reactive dyes produces in particular on cellulose fiber materials, for example cotton, strong yellow dyeings and prints having good fastness properties, of which in particular the good light, wet light and perspiration light fastness properties may be singled out.

EXAMPLE 9

A suspension of 9 parts of 3-(1,3-dichloroisopropylsulfonyl)aniline in a mixture of 40 parts by volume of acetone, 80 parts of water and 16 parts by volume of concentrated aqueous hydrochloric acid is diazotized in a conventional manner by the addition of sodium nitrite. Then a neutral solution of sodium salt of 7.9 parts of 1-(4'-sulfophenyl)-3-carboxypyrazol-5-one in 55 parts of water is added and a pH of 4 is set with sodium acetate. After the coupling reaction, which is carried out in a conventional manner at 15° C. to 20° C., has ended, the novel azo compound obtained is isolated by salting out with sodium chloride and filtration.

and shows very good fiber reactive dye properties. Applied by the application and fixing methods known for fiber reactive dyes it produces on the materials mentioned in the description, in particular on cellulose fiber materials, for example cotton, strong yellow dyeings and prints having good fastness properties, of which in particular the light, wet light and perspiration light fastness properties may be singled out.

EXAMPLES 10 TO 59

The Table Examples which follow describe further novel azo compounds conforming to the formula (1) in terms of the components indicated in the particular Table Example, of which $D^1$, $D^2$ and $D^3$ have the following meanings:

$D^1$ = 4-(1',3'-dichloroisopropylsulfonyl)phenyl
$D^2$ = 3-(1',3'-dichloroisopropylsulfonyl)phenyl
$D^3$ = 4-(1'-chloro-3'-acetyloxyisopropylsulfonyl)phenyl. These azo compounds according to the invention can be prepared from the diazo and coupling components evident from the Table Example in a manner according to the invention, for example analogously to one of the above Embodiment Examples. They have very good fiber reactive dye properties and applied by the application and fixing methods customary for fiber reactive dyes dye in particular cellulose fiber materials with good fastness properties in the hue indicated for the particular Table Example.

| | Azo compound of formula (1) | | |
|---|---|---|---|
| Example | Radical D | Radical K | Hue |
| 10 | $D^1$ | 1-(4'-$\beta$-sulfatoethylsulfonyl-phenyl)-3-methylpyrazol-5-on-4-yl | yellow (418) |
| 11 | $D^2$ | 1-(4'-$\beta$-sulfatoethylsulfonyl-phenyl)-3-methylpyrazol-5-on-4-yl | yellow (415) |
| 12 | $D^1$ | 1-(4'-$\beta$-sulfatoethylsulfonyl-phenyl)-3-carboxypyrazol-5-on-4-yl | yellow (419) |
| 13 | $D^2$ | 1-(4'-$\beta$-sulfatoethylsulfonyl-phenyl)-3-carboxypyrazol-5-on-4-yl | yellow (407) |
| 14 | $D^1$ | 1-(4'-sulfophenyl)-3-methyl-pyrazol-5-on-4-yl | yellow (421) |
| 15 | $D^2$ | 1-(4'-sulfophenyl)-3-methyl-pyrazol-5-on-4-yl | yellow (419) |
| 16 | $D^1$ | 3-acetylamino-6-sulfo-8-hydroxy-naphth-7-yl | yellowish orange (480) |
| 17 | $D^1$ | 2-benzoylamino-6-sulfo-8-hydroxy-naphth-7-yl | red (491) |
| 18 | $D^1$ | 2-(N-methyl-N-acetyl)amino-6-sulfo-8-hydroxynaphth-7-yl | orange (495) |
| 19 | $D^1$ | 1-acetylamino-3,6-disulfo-8-hydroxynaphth-7-yl | red (498) |
| 20 | $D^1$ | 1-benzoylamino-4,6-disulfo-8- | red |

-continued

| Example | Radical D | Radical K | Hue |
|---|---|---|---|
| | | hydroxynapthth-7-yl | (499) |
| 21 | D¹ | 1-benzoylamino-3,6-disulfo-8-hydroxynaphth-7-yl | red (500) |
| 22 | D¹ | 1-acetylamino-4,6-disulfo-8-hydroxynaphth-7-yl | red (497) |
| 23 | D¹ | 3,6-disulfo-2-hydroxynaphth-1-yl | orange (483) |
| 24 | D² | 2-acetylamino-5-sulfo-4-aminophenyl | yellow (408) |
| 25 | D¹ | 2-benzoylamino-5-sulfo-4-aminophenyl | yellow (411) |
| 26 | D² | 2-benzoylamino-5-sulfo-4-aminophenyl | yellow (410) |
| 27 | D¹ | 2-ureido-5-aminophenyl | yellow (390) |
| 28 | D² | 2-ureido-5-aminophenyl | yellow (388) |
| 29 | D³ | 2-acetylamino-6-sulfo-8-hydroxynaphth-7-yl | orange (489) |
| 30 | D² | 3-acetylamino-6-sulfo-8-hydroxynaphth-7-yl | yellowish orange (477) |
| 31 | D² | 2-benzoylamino-6-sulfo-8-hydroxynaphth-7-yl | orange (489) |
| 32 | D² | 2-(N-methyl-N-acetyl)amino-6-sulfo-8-hydroxynaphth-7-yl | orange (492) |
| 33 | D² | 1-acetylamino-3,6-disulfo-8-hydroxynaphth-7-yl | red (470) |
| 34 | D² | 1-benzoylamino-4,6-disulfo-8-hydroxynaphth-7-yl | red (497) |
| 35 | D² | 1-benzoylamino-3,6-disulfo-8-hydroxynaphth-7-yl | red (497) |
| 36 | D² | 1-acetylamino-3,6-disulfo-8-hydroxynaphth-7-yl | red (498) |
| 37 | D² | 3,6-disulfo-2-hydroxynaphth-1-yl | orange (496) |
| 38 | D² | 2-acetylamino-5-sulfo-4-aminophenyl | yellow (480) |
| 39 | D¹ | 4-[N,N-di-(β-hydroxyethyl)]-aminophenyl | yellow |
| 40 | D² | 4-[N,N-di-(β-hydroxyethyl)]-aminophenyl | yellow (430) |
| 41 | D² | 2-chloro-4-[N,N-di-(β-sulfatoethyl)]aminophenyl | yellow (420) |
| 42 | D¹ | 4-[N,N-di-β-sulfatoethyl)]-aminophenyl | yellow (432) |
| 43 | D² | 4-[N,N-di-β-sulfatoethyl)]-aminophenyl | yellow (430) |
| 44 | D¹ | 2-chloro-5-methoxy-4-[N,N-di-(β-hydroxyethyl)]aminophenyl | orange-yellow (437) |
| 45 | D² | 2-chloro-5-methoxy-4-[N,N-di-(β-hydroxyethyl)]aminophenyl | orange-yellow (435) |
| 46 | D² | 2-[4'-(β-sulfatoethylsulfonyl)-phenyl]azo-1-amino-3,6-disulfo-8-hydroxynaphth-7-yl | navy (593) |
| 47 | D¹ | 2-4'-(β-sulfophenyl)azo-1-amino-3,6-disulfo-8-hydroxynaphth-7-yl | navy (596) |
| 48 | D² | 2-4'-(β-sulfophenyl)azo-1-amino-3,6-disulfo-8-hydroxynaphth-7-yl | navy (594) |
| 49 | D¹ | 2-(2',5'-disulfophenyl)azo-1-amino-3,6-disulfo-8-hydroxynaphth-7-yl | navy (590) |
| 50 | D² | 2-(2',5'-disulfophenyl)azo-1-amino-3,6-disulfo-8-hydroxynaphth-7-yl | navy (588) |
| 51 | D² | N-(β-sulfoethyl)-4-methyl-2-hydroxypyrid-6-on-3-yl | yellow (407) |
| 52 | D¹ | 1-N-ethyl-4-methyl-5-carbamoyl-2-hydroxypyrid-6-on-3-yl | yellow (404) |
| 53 | D² | 1-N-ethyl-4-methyl-5-carbamoyl-2-hydroxypyrid-6-on-3-yl | yellow (402) |
| 54 | D¹ | N-ethyl-4-methyl-5-sulfomethyl-2-hydroxypyrid-6-on-3-yl | yellow (408) |
| 55 | D² | N-ethyl-4-methyl-5-sulfomethyl-2-hydroxypyrid-6-on-3-yl | yellow (406) |
| 56 | D¹ | N-ethyl-4-methyl-5-cyano- | yellow |

-continued

| Example | Radical D | Radical K | Hue |
|---|---|---|---|
| | | 2-hydroxypyrid-6-on-3-yl | (405) |
| 57 | D² | N-ethyl-4-methyl-5-cyano-2-hydroxypyrid-6-on-3-yl | yellow (403) |
| 58 | D¹ | N-ethyl-4-methyl-5-sulfo-2-hydroxypyrid-6-on-3-yl | yellow (404) |
| 59 | D² | N-ethyl-4-methyl-5-sulfo-2-hydroxypyrid-6-on-3-yl | yellow (402) | what is claimed is:

1. A water soluble azo compound conforming to the formula (1)

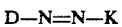

where
D is a radical of the formula (2), (2a) or (2b)

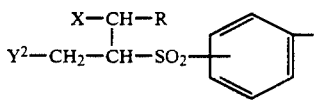 (2)

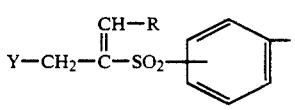 (2a)

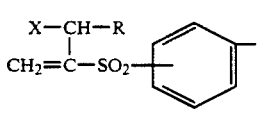 (2b)

where
Y is a substituent which is eliminable by alkali to form a vinyl group,
$Y^2$ has one of the meanings of Y or is hydroxy,
X is chlorine or bromine and
R is hydrogen, alkyl of from 1 to 4 carbon atoms, phenyl or halogen;
K is a radical of a singly couplable coupling component which may additionally contain an azo group, or the radical of a doubly couplable coupling component each selected from the series of the aminobenzenes, the phenols, the naphthols, the aminonaphthols or the acylaminonaphthols, having the acyl radical of an alkane- or alkenecarboxylic acid having from 1 to 4 or from 2 to 4 carbon atoms in the alkyl or alkenyl radical respectively or of an aromatic carboxylic acid or of an aromatic sulfonic acid or of an N-substituted carbamic acid, or from the series of the dihydroxynaphthalenesulfonic acids, the phenylazo- and naphthylazo-aminonaphtholsulfonic acids, the 5-pyrazolones and 5-aminopyrazoles, the acetoacetylarylides, the 2-hydroxy-6-pyridones and the hydroxyquinolines, and K may also contain a fiber reactive group of the formula $-SO_2-Y^1$, where $Y^1$ is vinyl or a group of the formula $-CH_2-CH_2-Y$, where Y has one of the above meanings.

2. An azo compound as claimed in claim 1, wherein K is a radical of the formula (3c), (3f), (3h), (3i), (3p) or (3q)

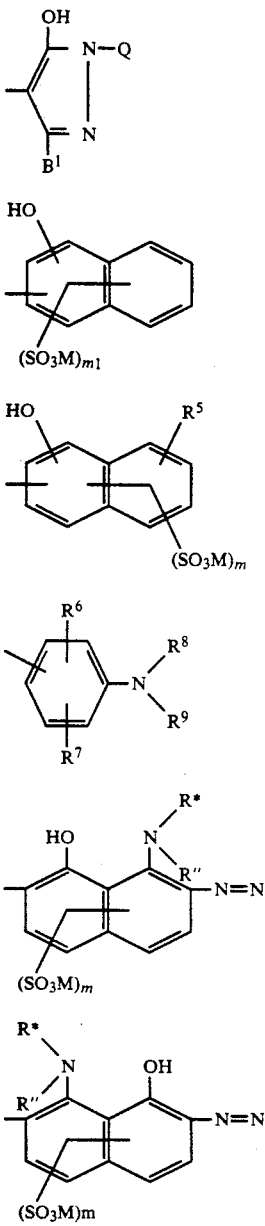

where

M is hydrogen or an alkali metal, $B^1$ is alkyl of from 1 to 4 carbon atoms, carboxy, carbalkoxy of from 2 to 5 carbon atoms, carbamoyl, phenyl or phenyl which is substituted by 1 or 2 substituents selected from the group consisting of sulfo, carboxy, methyl, ethyl, methoxy, ethoxy and chlorine;

Q is phenyl unsubstituted or substituted by 1, 2 or 3 substituents selected from the group consisting of chlorine, bromine, methyl, ethyl, methoxy, ethoxy, carboxy, sulfo and alkanoylamino of from 2 to 5 carbon atoms and/or by a group of the formula —$SO_2Y^1$, where $Y^1$ is vinyl or an ethyl group which contains an alkali-eliminable substituent in the β-position;

R* is hydrogen or alkyl of from 1 to 4 carbon atoms, unsubstituted or substituted by phenyl or by phenyl which is substituted by sulfo and/or by a group of the formula —$SO_2$—$Y^1$, where $Y^1$ is as defined above, or is alkanoyl of from 2 to 5 carbon atoms, phenylsulfonyl, benzoyl or sulfobenzoyl;

R" is hydrogen or alkyl of from 1 to 4 carbon atoms, unsubstituted or substituted by phenyl, sulfophenyl or a group of the formula —$SO_2$—$Y^1$, where $Y^1$ is as defined above, or is phenyl, or phenyl substituted by 1 or 2 substituents selected from the group consisting of alkyl of from 1 to 4 carbon atoms, alkoxy of from 1 to 4 carbon atoms, chlorine, bromine, sulfo and —$SO_2$—$Y^1$ where $Y^1$ is as defined above;

$R^5$ is phenylureido, whose phenyl is unsubstituted or substituted by a group of the formula —$SO_2$—$Y^1$, where $Y^1$ is as defined above, or is alkanoylamino of from 2 to 5 carbon atoms, unsubstituted or substituted in the alkyl radical by a group of the formula —$SO_2$—$Y^1$, where $Y^1$ is as defined above, or is alkenoylamino of from 3 to 5 carbon atoms, or is benzoylamino unsubstituted or substituted by substituents selected from the group consisting of chlorine, methyl, methoxy, nitro, sulfo, carboxy and —$SO_2$—$Y^1$, where $Y^1$ is as defined above;

$R^6$ is hydrogen, alkyl of from 1 to 4 carbon atoms, alkoxy of from 1 to 4 carbon atoms, sulfo, carboxy, carbalkoxy of from 2 to 5 carbon atoms, halogen or alkoxy of from 1 to 4 carbons unsubstituted or substituted by hydroxy, acetyloxy, carboxy, carbamoyl, cyano or halogen;

$R^7$ is hydrogen, alkyl of from 1 to 4 carbon atoms, alkoxy of from 1 to 4 carbon atoms, halogen, cyano, trifluoromethyl, alkoxy of from 1 to 4 carbon atoms, which is substituted by hydroxy, acetyloxy, carboxy, carbamoyl, cyano or halogen or by a group of the formula —$SO_2$—$Y^1$, where $Y^1$ is as defined above, or is alkanoylamino of from 2 to 5 carbon atoms, unsubstituted or substituted by chlorine, bromine, alkoxy of from 1 to 4 carbon atoms, phenoxy, phenyl, hydroxy, carboxy or sulfo or a group of the formula —$SO_2$—$Y^1$, where $Y^1$ is as defined above, or is alkenoylamino of from 3 to 5 carbon atoms, unsubstituted or substituted by chlorine, bromine, carboxy or sulfo, or is benzoylamino, unsubstituted or substituted in the benzene nucleus by substituents selected from the group consisting of chlorine, methyl, sulfo and a group of the formula —$SO_2$—$Y^1$, where $Y^1$ is as defined above, or is alkylsulfonyl of from 1 to 4 carbon atoms or phenylsulfonyl, unsubstituted or substituted in the benzene nucleus by substituents selected from the group consisting of chlorine, methyl, sulfo and a group of the formula —$SO_2$—$Y^1$, where $Y^1$ is as defined above, or is alkylsulfonylamino of from 1 to 4 carbon atoms, unsubstituted or substituted by hydroxy, sulfato, chlorine, bromine, alkoxy of from 1 to 4 carbon atoms or a group of the formula —$SO_2$—$Y^1$, where $Y^1$ is as defined above, or is phenylsulfonylamino, unsubstituted or substituted in the benzene nucleus by substituents selected from the group consisting of chlorine, methyl, sulfo and a group of the formula —$SO_2$—$Y^1$, where $Y^1$ is as defined above, or is carbamoyl or carbamoyl monosubstituted or disubstituted on the nitrogen atom by 1 or 2 substituents, which substituents belong to the group consisting of alkyl of from 1 to 4 carbon atoms, alkyl of from 1 to 4 carbon atoms which is substituted by hydroxy, sulfo, carboxy, sulfato, phenyl or a group of the formula —$SO_2$—$Y^1$, where $Y^1$ is as defined above, cycloalkyl of from 5 to 8 carbon atoms, phenyl and phenyl which is substituted by substituents selected from the group consisting of chlorine, sulfo, methyl, methoxy, carboxy and a group of the formula —SO$_2$—Y$^1$, where Y$^1$ is as defined above, or is sulfamoyl or sulfamoyl mono- or disubstituted on the nitrogen atom by 1 or 2 substituents, which substituents belong to the group consisting of alkyl of from 1 to 4 carbon atoms, alkyl of from 1 to 4 carbon atoms which is substituted by hydroxy, sulfo, carboxy, sulfato, phenyl or a group of the formula —SO$_2$—Y$^1$, where Y$^1$ is as defined above, cycloalkyl of from 5 to 8 carbon atoms, phenyl and phenyl which is substituted by substituents selected from the group consisting of chlorine, sulfo, methyl, methoxy, carboxy and a group of the formula —SO$_2$—Y$^1$, where Y$^1$ is as defined above, or is ureido or ureido which is mono- or disubstituted at the terminal nitrogen atom by 1 or 2 substituents, which substituents belong to the group consisting of alkyl of from 1 to 4 carbon atoms, alkyl of from 1 to 4 carbon atoms which is substituted by hydroxy, sulfo, carboxy, sulfato, phenyl or a group of the formula —SO$_2$—Y$^1$, where Y$^1$ is as defined above, cycloalkyl of from 5 to 8 carbon atoms, phenyl and phenyl which is substituted by substituents selected from the group consisting of chlorine, sulfo, methyl, methoxy, carboxy and a group of the formula —SO$_2$—Y$^1$, where Y$^1$ is as defined above;

R$^8$ is hydrogen or alkyl of from 1 to 4 carbon atoms, unsubstituted or substituted by hydroxy, sulfo, carboxy, sulfato, a group of the formula —SO$_2$—Y$^1$, where Y$^1$ is as defined above, phenyl or sulfophenyl, or is alkenyl of from 2 to 4 carbon atoms, unsubstituted or substituted by carboxy, sulfo, chlorine or bromine, or is cycloalkyl of from 5 to 8 carbon atoms;

R$^9$ is hydrogen or alkyl of from 1 to 4 carbon atoms, unsubstituted or substituted by hydroxy, sulfo, carboxyl, sulfato, phenyl or —SO$_2$—Y$^1$, where Y$^1$ is as defined above, or is alkenyl of from 2 to 5 carbon atoms, unsubstituted or substituted by carboxy, sulfo or —SO$_2$—Y$^1$, where Y$^1$ is as defined above, or by chlorine or bromine, or R$^9$ is cycloalkyl of from 5 to 8 carbon atoms or phenyl, unsubstituted or substituted by substituents selected from the group consisting of chlorine, sulfo, methyl, methoxy, carboxy and —SO$_2$—Y$^1$, where Y$^1$ is as defined above, or is naphthyl which is substituted by 1, 2 or 3 sulfo groups or by 1 or 2 sulfo groups and 1 or 2 groups of the formula —SO$_2$—Y$^1$, where Y$^1$ is as defined above, or only by one such group —SO$_2$—Y$^1$, or R$^8$ and R$^9$ together with the nitrogen atom are N-piperidino, N-morpholino or N-piperazino;

m is 1 or 2;

m$_1$ is 1, 2 or 3;

D* is a group of the formula (2), (2a) or (2b) as defined in claim 1 or is phenyl unsubstituted or substituted by 1, 2 or 3 substituents selected from the group consisting of alkyl of from 1 to 4 carbon atoms, alkoxy of from 1 to 4 carbon atoms, chlorine, bromine, hydroxy, carboxy, sulfo, carbamoyl, sulfamoyl and alkanoylamino of from 2 to 5 carbon atoms and/or by a group of the formula —SO$_2$—Y$^1$, where Y$^1$ is as defined above, or D* is naphthyl which is substituted by 1, 2 or 3 sulfo groups or by 1 or 2 sulfo groups and 1 or 2 groups of the formula —SO$_2$—Y$^1$, where Y$^1$ is as defined above, or only by one such group —SO$_2$—Y$^1$, it being possible for D and D* to have meanings identical to or different from each other.

3. An azo compound as claimed in claim 1, wherein K is a radical of the formula (3d), (3e), 3(k) or (3m)

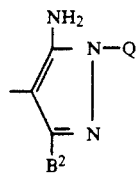

(3d)

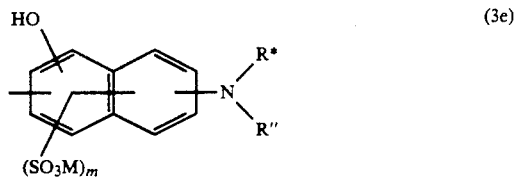

(3e)

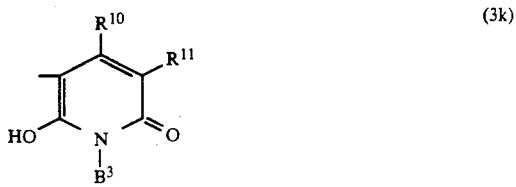

(3k)

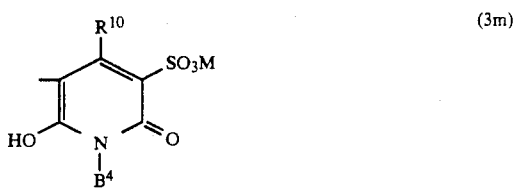

(3m)

where

M is hydrogen or an alkali metal;

B$^2$ is alkyl of from 1 to 4 carbon atoms, carbalkoxy of from 2 to 5 carbon atoms, carbamoyl, phenyl or phenyl which is substituted by 1 or 2 substituents selected from the group consisting of alkyl of from 1 to 4 carbon atoms, alkoxy of from 1 to 4 carbon atoms, chlorine, bromine and sulfo;

Q is phenyl, or phenyl substituted by 1, 2 or 3 substituents selected from the group consisting of chlorine, bromine, methyl, ethyl, methoxy, ethoxy, carboxyl, sulfo and alkanoylamino of from 2 to 5 carbon atoms and/or by a group of the formula —SO$_2$—Y$^1$, where Y$^1$ is vinyl or an ethyl group which contains an alkali eliminable substituent in the β-position;

R* is hydrogen or alkyl of from 1 to 4 carbon atoms, unsubstituted or substituted by phenyl or by phenyl which is substituted by sulfo and/or a group of the formula —SO$_2$—Y$^1$, where Y$^1$ is as defined above, or is alkanoyl of from 2 to 5 carbon atoms, phenylsulfonyl, benzoyl or sulfobenzoyl;

R″ is hydrogen or alkyl of from 1 to 4 carbon atoms, unsubstituted or substituted by phenyl, sulfophenyl or a group of the formula —SO$_2$—Y$^1$, where Y$^1$ is as defined above, or is phenyl, or phenyl substituted by 1 or 2 substituents selected from the group consisting of alkyl of from 1 to 4 carbon atoms, alkoxy of from 1 to 4 carbon atoms, chlorine, bromine, sulfo and —SO$_2$—Y$^1$, where Y$^1$ is as defined above;

m is 1 or 2;

B$^3$ is hydrogen or alkyl from 1 to 4 carbon atoms, unsubstituted or substituted by phenyl, sulfo, sulfophenyl or a group —SO$_2$—Y$^1$, where Y$^1$ is as defined in claim 1;

$R^{10}$ is hydrogen or alkyl of from 1 to 4 carbon atoms or alkyl of from 1 to 4 carbon atoms which is substituted by alkoxy of from 1 to 4 carbon atoms or cyano;

$R^{11}$ is hydrogen, carboxy, sulfo, sulfoalkyl having an alkylene radical of from 1 to 4 carbon atoms, cyano or carbamoyl;

$B^4$ is hydrogen, alkyl of from 1 to 4 carbon atoms or alkyl of from 1 to 4 carbon atoms which is substituted by alkoxy of from 1 to 4 carbon atoms, sulfo, carboxy, sulfato, phenyl, sulfophenyl, acetylamino, benzoylamino, cyano or a group of the formula $-SO_2-Y^1$, where $Y^1$ is as defined above, or is alkenyl of from 2 to 4 carbon atoms, cyclohexyl, phenyl or phenyl which is substituted by substituents selected from the group consisting of carboxy, sulfo, benzoylamino, acetylamino, $-SO_2-Y^1$, where $Y^1$ is as defined above, and chlorine.

4. An azo compound as claimed in claim 2, wherein K is a radical of the formula (3c) or (3i) where $B^1$ is methyl, carboxy or carbalkoxy of from 2 to 5 carbon atoms, Q is phenyl which is substituted by sulfo and/or a group of the formula $-SO_2-Y^1$, where $Y^1$ is as defined in claim 2, $R^6$ is hydrogen, sulfo, methyl, ethyl, methoxy or ethoxy;

$R^7$ is hydrogen, methyl, ethyl, methoxy, ethoxy, chlorine, amino, substituted amino, alkanoylamino of from 2 to 5 carbon atoms, benzoylamino or phenylsulfonylamino, $R^8$ is hydrogen, methyl, ethyl or hydroxy-, sulfo-, sulfato- or carboxy-substituted alkyl of from 2 to 4 carbon atoms, and $R^9$ is hydrogen, methyl, ethyl or alkyl of from 2 to 4 carbon atoms, which is substituted by hydroxy, sulfo, sulfato or carboxy.

5. An azo compound as claimed in claim 3, wherein K is a radical of the formula (3e), (3k) or (3m) where $R^*$ is acetyl, sulfobenzoyl or benzoyl, $R''$ is hydrogen or alkyl of from 1 to 4 carbon atoms, m is 1 or 2, M is hydrogen or an alkali metal, $R^{10}$ is hydrogen or methyl, $R^{11}$ is hydrogen, cyano, sulfomethyl, carbamoyl or carboxy, $B^3$ is hydrogen, ethyl or sulfo-, phenyl- or sulfophenyl-substituted alkyl of 2 to 4 carbon atoms, and $B^4$ is hydrogen, methyl, ethyl or sulfo-, phenyl- or sulfophenyl-substituted alkyl of 2 to 4 carbon atoms.

6. An azo compound as claimed in claim 2, wherein K is a radical of the formula (3p) where $R^*$ is acetyl, sulfobenzoyl or benzoyl or hydrogen, $R''$ is alkyl of from 1 to 4 carbon atoms or hydrogen, m is 2, and M is hydrogen or an alkali metal.

7. An azo compound as claimed in claim 1, wherein R is hydrogen.

8. An azo compound as claimed in claim 1, wherein X is chlorine.

9. An azo compound as claimed in claim 1, wherein Y is sulfato.

10. An azo compound as claimed in claim 1, wherein D is a radical of the formula (2).

11. An azo compound as claimed in claim 1, wherein Y is chlorine.

12. An azo compound as claimed in claim 2, wherein X is chlorine.

13. An azo compound as claimed in claim 2, wherein D is a radical of the formula (2).

14. An azo compound as claimed in claim 2, wherein Y is sulfato or chlorine.

15. An azo compound according to claim 2, wherein $R^*$ and $R''$ are both hydrogen.

16. An azo compound according to claim 3, wherein $R^*$ and $R''$ are both hydrogen.

* * * * *